(12) United States Patent
Takashima

(10) Patent No.: US 11,707,415 B2
(45) Date of Patent: Jul. 25, 2023

(54) MEDICINE MANAGEMENT SYSTEM

(71) Applicant: FUJIFILM Toyama Chemical Co., Ltd., Tokyo (JP)

(72) Inventor: Masanobu Takashima, Tokyo (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 113 days.

(21) Appl. No.: 17/512,058

(22) Filed: Oct. 27, 2021

(65) Prior Publication Data

US 2022/0047462 A1 Feb. 17, 2022

Related U.S. Application Data

(63) Continuation of application No. PCT/JP2020/019574, filed on May 18, 2020.

(30) Foreign Application Priority Data

May 30, 2019 (JP) .................................. 2019-101352

(51) Int. Cl.
*A61J 7/04* (2006.01)
*G16H 20/10* (2018.01)

(52) U.S. Cl.
CPC ........... *A61J 7/0427* (2015.05); *A61J 7/0481* (2013.01); *G16H 20/10* (2018.01); *A61J 2205/30* (2013.01)

(58) Field of Classification Search
CPC .... A61J 7/0427; A61J 2205/30; A61J 7/0481; G16H 20/10
See application file for complete search history.

(56) References Cited

U.S. PATENT DOCUMENTS 7,451,876 B2 * 11/2008 Bossi ...................... A61J 1/035
206/488
7,956,894 B2 * 6/2011 Akers .................... G16H 30/20
348/231.2

(Continued)

FOREIGN PATENT DOCUMENTS

CN 103473625 A 12/2013
CN 104887527 A 9/2015

(Continued)

OTHER PUBLICATIONS

Extended European Search Report dated Jun. 28, 2022 for corresponding Application No. 20813493.2.

(Continued)

*Primary Examiner* — Michael Collins
(74) *Attorney, Agent, or Firm* — Birch, Stewart, Kolasch & Birch, LLP

(57) ABSTRACT

There is provided a medicine management system capable of checking a receipt status and a dosage stage of delivered medicines even at a delivery source. The medicine management system includes a management server for managing a receipt status and a dosage status of medicines to be delivered, a first terminal having a function of notifying the management server of information indicating receipt of medicines when the medicines have been received, a second terminal having a function of notifying the management server of information indicating dosage of medicines when the medicines have been taken, and a third terminal having a function of acquiring from the management server and displaying information on a receipt status and a dosage status of medicines.

16 Claims, 16 Drawing Sheets

(56) References Cited

U.S. PATENT DOCUMENTS

| | | | | |
|---|---|---|---|---|
| 8,019,471 B2* | 9/2011 | Bogash | ............... | G16H 20/13 |
| | | | | 700/242 |
| 8,738,177 B2* | 5/2014 | van Ooyen | ............ | G07F 11/44 |
| | | | | 700/235 |
| 9,272,796 B1* | 3/2016 | Chudy | ............... | G01N 21/9508 |
| 11,568,537 B2* | 1/2023 | Sandmann | ............ | G01G 23/37 |
| 2006/0060645 A1* | 3/2006 | Udaka | .................. | G06Q 10/00 |
| | | | | 235/375 |
| 2011/0202366 A1* | 8/2011 | Akers | .................. | G16H 20/10 |
| | | | | 705/2 |
| 2013/0194414 A1 | 8/2013 | Poirier et al. | | |
| 2020/0098462 A1 | 3/2020 | Takashima et al. | | |

FOREIGN PATENT DOCUMENTS

| | | |
|---|---|---|
| CN | 106023466 A | 10/2016 |
| CN | 109044849 A | 12/2018 |
| CN | 113139773 A | 7/2021 |
| JP | 2016-179161 A | 10/2016 |
| JP | 2017-120630 A | 7/2017 |
| TW | 200513926 A | 4/2005 |
| WO | WO 2015/060296 A1 | 4/2015 |
| WO | WO 2018/221167 A1 | 12/2018 |

OTHER PUBLICATIONS

International Preliminary Report on Patentability and English translation of the Written Opinion of the International Searching Authority (Forms PCT/IB/326, PCT/IB/373 and PCT/ISA/237) for International Application No. PCT/JP2020/019574, dated Dec. 9, 2021.
International Search Report (Form PCT/ISA/210) for International Application No. PCT/JP2020/019574, dated Jul. 21, 2020, with English translation.
Office Action for corresponding Application No. 2020800384113 dated Nov. 30, 2022, with English translation.

* cited by examiner

| PATIENT NAME | TARO FUJI | TARO FUJI | ... | HANAKO FUJI |
|---|---|---|---|---|
| AGE | 73 YEARS AND 5 MONTHS | 73 YEARS AND 5 MONTHS | | 70 YEARS AND 2 MONTHS |
| GENDER | MALE | MALE | | FEMALE |
| ADMITTING FACILITY NAME | A FACILITY | A FACILITY | | A FACILITY |
| USER ID OF PORTABLE TERMINAL | AXXXX1 | AXXXX1 | | AXXXX1 |
| DELIVERY IDENTIFICATION INFORMATION | xxxxxxx01 | xxxxxxx01 | ... | xxxxxxx01 |
| MEDICINE IDENTIFICATION INFORMATION | AxxxxBxx001 | AxxxxBxx002 | | AxxxxCxx001 |
| MEDICINE NAME | A CAPSULE<br>B TABLET<br>C TABLET<br>D TABLET<br>E TABLET | A CAPSULE<br>B TABLET<br>C TABLET<br>D TABLET<br>E TABLET | | F TABLET<br>G TABLET<br>H TABLET |
| DOSAGE TIMING | AFTER BREAKFAST | AFTER BREAKFAST | | AFTER BREAKFAST |
| RECEIPT STATUS | RECEIVED | RECEIVED | | RECEIVED |
| DOSAGE STATUS | TAKEN | UNTAKEN | | TAKEN |

MEDICINE MANAGEMENT SYSTEM

CROSS-REFERENCE TO RELATED APPLICATIONS

The present application is a Continuation of PCT International Application No. PCT/JP2020/019574 filed on May 18, 2020 claiming priority under 35 U.S.C § 119(a) to Japanese Patent Application No. 2019-101352 filed on May 30, 2019. Each of the above applications is hereby expressly incorporated by reference, in its entirety, into the present application.

BACKGROUND OF THE INVENTION

1. Field of the Invention

The present invention relates to a medicine management system, and relates to a medicine management system for managing a receipt status and a dosage status of delivered medicines.

2. Description of the Related Art

Generally, hospital pharmacies, pharmacies, etc. that respond to demands of prescriptions from nursing and caring facilities such as the Long-Term Care Health Facilities often deliver medicines for multiple people in a lump when delivering medicines prescribed for facility residents (patients) to the facilities.

As a delivery method for delivering medicines for multiple people to the same institution in a lump, International Publication No. WO 2015/060296 describes that medicines prescribed for a plurality of facility residents are individually packaged into bags on a dose basis, medicines which have been packaged on a dose basis (one-dose-packaged medicines) are stored in a lump in a medicine packet for each same dosage timing, and then delivered to the facilities. International Publication No. WO 2015/060296 also describes that a two-dimensional code obtained by encoding a dosage timing, delivery destination identification information and the like is printed on each medicine packet, and the printed two-dimensional code is read out at a delivery destination to check the presence or absence of a delivery error. Further, International Publication No. WO 2015/060296 describes that a two-dimensional code obtained by encoding ID of a person who takes a medicine, a dosage timing, delivery destination identification information and the like is printed on an individual one-dose-packaging bag (packaging bag), the printed two-dimensional code is read out when the medicine is dispensed, thereby checking a person who should take the medicines, and the readout is recorded to record a dosage history.

Here, "one-dose-packaging" means that a plurality of medicines to be taken by a patient are prepared to be separated and put into bags (packaging bags) on a dose basis for each dosage timing like a dosage after breakfast, a dosage after dinner or the like.

SUMMARY OF THE INVENTION

The invention described in International Publication No. WO 2015/060296 can check the presence or absence of a delivery error at a delivery destination by reading a two-dimensional code printed on a medicine packet. However, the invention has a drawback that a delivery source cannot check whether or not the delivered medicines have been correctly received at the delivery destination. Especially when the delivery source is a pharmacy, the pharmacy often responds to demands of prescriptions from a plurality of nursing and caring facilities, so that stricter check is required.

Further, the invention described in International Publication No. WO 2015/060296 can check a dosage history by reading the two-dimensional code printed on each packaging bag. However, the invention has a drawback that the delivery source cannot check whether or not the delivered medicines are taken correctly. Especially when the delivery source is a pharmacy, the pharmacy often responds to demands of prescriptions from a plurality of nursing and caring facilities, so that stricter check is required.

An object of the present invention, which has been made in view of such circumstances, is to provide a medicine management system capable of checking a receipt status and a dosage status of delivered medicines even at a delivery source.

(1) a medicine management system comprises: a management server configured to manage a receipt status and a dosage status of medicines to be delivered; a first terminal configured to have a function of notifying the management server of information indicating receipt of the medicines when the medicines have been received; a second terminal configured to have a function of notifying the management server of information indicating dosage of the medicines when the medicines have been taken; and a third terminal configured to have a function of acquiring from the management server and displaying information on a receipt status and a dosage status of the medicines, wherein the medicines include packaged medicines which are packaged on a dose basis based on prescription information, and unique delivery identification information is given to the medicines for each delivery, the delivery identification information is indicated on a delivery article to be delivered together with the medicines, unique medicine identification information is given to the packaged medicines on a package basis, and indicated on an individual packaging bag, the management server manages the medicine identification information in association with the delivery identification information and information extracted from the prescription information, the first terminal reads the delivery identification information indicated on the delivery article, and notifies the management server of information indicating the receipt, the second terminal reads the medicine identification information indicated on the packaging bag, and notifies the management server of information indicating the dosage of the medicines, and the management server receives a notification of the information indicating the receipt from the first terminal to manage the receipt status of the medicines, and receives a notification of the information indicating the dosage from the second terminal to manage the dosage status of the medicines.

According to the present aspect, the medicine management system comprises the management server for managing the receipt status and the dosage status of medicines to be delivered, the first terminal having the function of notifying the management server of the information indicating the receipt of medicines when the medicines have been received, the second terminal having the function of notifying the management server of the information indicating the dosage of medicines when the medicines have been taken, and the third terminal having the function of acquiring from the management server and displaying the information on the receipt status and the dosage status of medicines. The medicines include packaged medicines which are packaged on a dose basis based on prescription information. Further, unique delivery identification information is given to the medicines for each delivery. The delivery identification information is indicated on a delivery article to be delivered together with the medicines. Unique medicine identification information is given to the packaged medicines on a package basis, and indicated on an individual packaging bag. The management server manages the medicine identification information in association with the delivery identification information and information extracted from the prescription information. The first terminal reads the delivery identification information indicated on the delivery article, and notifies the management server of information indicating the receipt. The second terminal reads the medicine identification information indicated on the packaging bag, and notifies the management server of information indicating the dosage of the medicines. The management server receives a notification of the information indicating the receipt from the first terminal to manage the receipt status of the medicines. Further, the management server receives a notification of the information indicating the dosage from the second terminal to manage the dosage status of the medicines.

(2) In the medicine management system of the foregoing (1), the first terminal further has a function of acquiring from the management server and displaying the delivery identification information and information of the medicines scheduled to be delivered.

According to the present aspect, the first terminal further has the function of acquiring from the management server and displaying the delivery identification information and the information of the medicines scheduled to be delivered.

(3) In the medicine management system of the foregoing (1) or (2), the second terminal further has a function of acquiring from the management server and displaying information on a medicine taker who is scheduled to take a medicine.

According to the present aspect, the second terminal further has the function of acquiring from the management server and displaying information on a medicine taker who is scheduled to take a medicine.

(4) In the medicine management system of any one of the foregoing (1) to the foregoing (3), the second terminal further has a function of acquiring from the management server and displaying information on a dosage timing for each medicine taker.

According to the present aspect, the second terminal further has the function of acquiring from the management server and displaying the information on the dosage timing for each medicine taker.

(5) In the medicine management system according to any one of the foregoing (1) to the foregoing (4), the second terminal further has a function of acquiring from the management server and displaying information on a medicine taker for each dosage timing.

According to the present aspect, the second terminal further has the function of acquiring from the management server and displaying information on a medicine taker for each dosage timing.

(6) In the medicine management system according to one of the foregoing (1) to the foregoing (5), the second terminal identifies a medicine taker, read the medicine identification information, and notifies the management server of information indicating the medicine dosage.

According to the present aspect, the second terminal identifies a medicine taker, reads the medicine identification information, and notifies the management server of information indicating the medicine dosage.

(7) In the medicine management system according to one of the foregoing (1) to the foregoing (6), the second terminal reads medicine taker identification information unique to a medicine taker, reads the medicine identification information, and notifies the management server of information indicating the dosage.

According to the present aspect, the second terminal reads the medicine taker identification information unique to a medicine taker, reads the medicine identification information, and notifies the management server of information indicating the dosage.

(8) In the medicine management system according to one of the foregoing (1) to the foregoing (7), the delivery identification information is encoded and indicated on the delivery article.

According to the present aspect, the delivery identification information is encoded and indicated on the delivery article.

(9) In the medicine management system according to any one of the foregoing (1) to the foregoing (8), the medicine identification information is encoded and indicated on the packaging bag.

According to the present aspect, the medicine identification information is encoded and indicated on the packaging bag.

(10) In the medicine management system according to the foregoing (1) to the foregoing (9), the first terminal also serves as the second terminal.

According to the present aspect, the first terminal also serves as the second terminal. In other words, the functions of the first terminal and the second terminal are implemented by one terminal.

(11) The medicine management system according to any one of the foregoing (1) to the foregoing (10), further comprises a one-dose-packaging audit support device that includes an imaging unit configured to image the packaged medicines on a package basis, an audit support unit configured to support audit of the packaged medicines based on images captured by the imaging unit and the prescription information, and a medicine identification information giving unit configured to give, on a package basis, the medicine identification information to the packaged medicines for which audit has been completed.

According to the present aspect, the one-dose-packaging audit support device is further provided. The one-dose-packaging audit support device includes the imaging unit for imaging the packaged medicines on a package basis, the audit support unit for supporting audit of the packaged medicines based on images captured by the imaging unit and the prescription information, and the medicine identification information giving unit for giving, on a package basis, the medicine identification information to the packaged medicines for which audit has been completed.

(12) In the medicine management system of the foregoing (11), the one-dose-packaging audit support device further includes a medicine identification information transmission unit for transmitting the medicine identification information to the management server in association with information extracted from the prescription information.

According to the present aspect, the one-dose-packaging audit support device further includes the medicine identification information transmission unit. The medicine identification information transmission unit transmits the medicine identification information to the management server in association with the information extracted from the prescription information.

(13) In the medicine management system of the foregoing (11) or (12), the one-dose-packaging audit support device further includes a delivery identification information giving unit configured to give the delivery identification information, and a delivery identification information transmitting unit configured to transmit the medicine identification information to the management server in association with the delivery identification information.

According to the present aspect, the one-dose-packaging audit support device further includes a delivery identification information giving unit and a delivery identification information transmitting unit. The delivery identification information giving unit gives the delivery identification information. The delivery identification information transmitting unit transmits the medicine identification information to the management server in association with the delivery identification information.

(14) In the medicine management system of the foregoing (13), the one-dose-packaging audit support device further includes a printing unit configured to print the delivery identification information.

According to the present aspect, the one-dose-packaging audit support device further includes the printing unit for printing the delivery identification information.

(15) In the medicine management system according to any one of the foregoing (11) to the foregoing (14), the one-dose-packaging audit support device also serves as the third terminal.

According to the present aspect, the one-dose-packaging audit support device also serve as the third terminal. In other words, the one-dose-packaging audit support device is provided with the function of the third terminal.

(16) In the medicine management system according to any one of the foregoing (1) to the foregoing (15), the management server manages a receipt status and a dosage status of medicines to be delivered from a pharmacy or a hospital pharmacy.

According to the present aspect, the management server manages the receipt status and the dosage status of medicines to be delivered from a pharmacy or a hospital pharmacy.

According to the present invention, the receipt status and the dosage status of delivered medicines can be checked even at a delivery source.

BRIEF DESCRIPTION OF THE DRAWINGS

FIG. 5 is a diagram showing an example of a display of a collation result.

FIG. 8 is a diagram showing an example of a management database.

DESCRIPTION OF THE PREFERRED EMBODIMENTS

Preferred embodiments according to the present invention will be described hereunder with reference to the accompanying drawings.

[Schematic Configuration of Medicine Management System]

Figure 1:
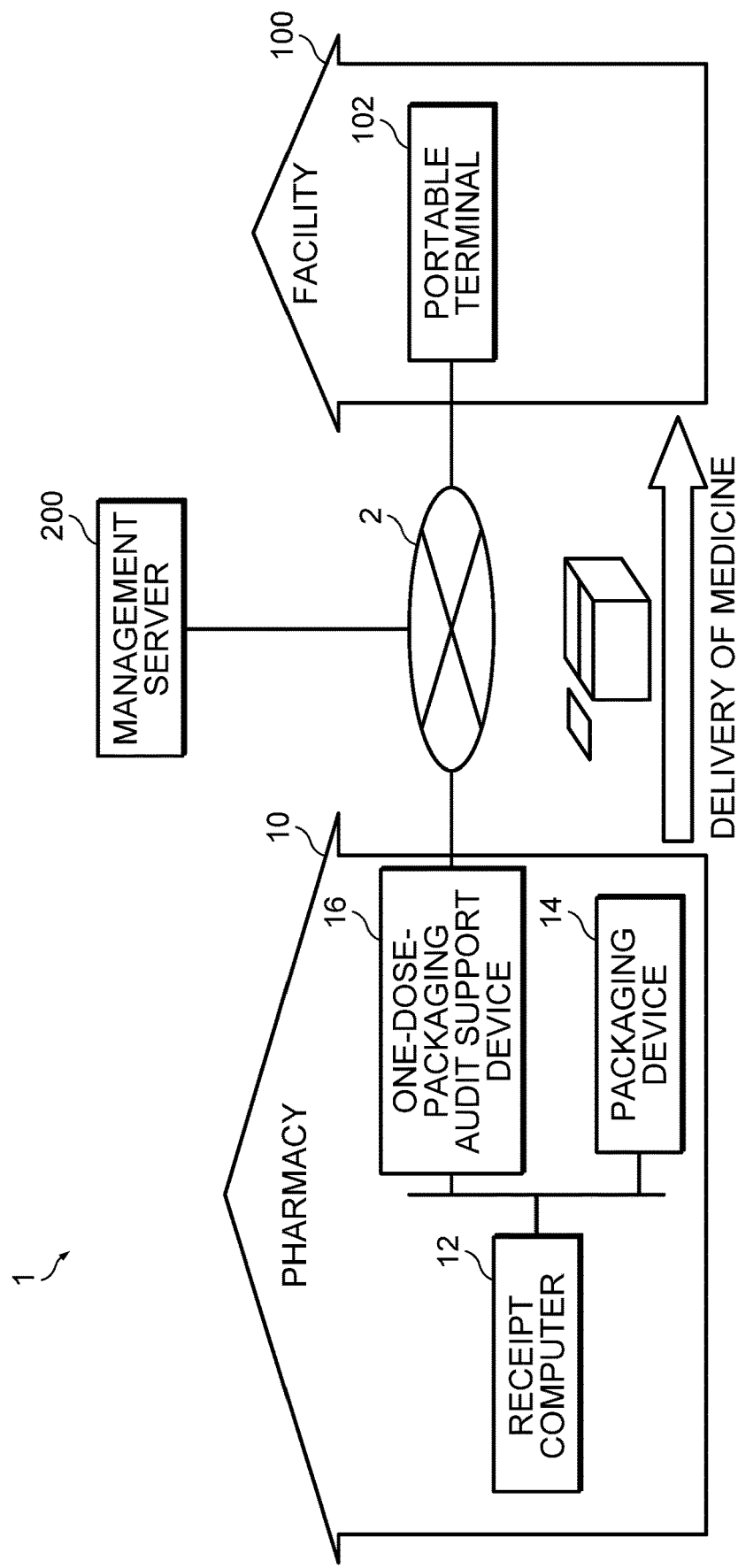
FIG. 1 is a system configuration diagram showing an embodiment of a medicine management system according to the present invention.

FIG. 1 is a system configuration diagram showing an embodiment of a medicine management system according to the present invention.

A medicine management system 1 of the present embodiment is configured as a system for managing a receipt status and a dosage status of medicines delivered from a pharmacy 10 such as a dispensing pharmacy to a facility 100 such as Long-Term Care Health Facilities. The medicines to be delivered from the pharmacy 10 include at least packaged medicines, which are one-dose-packaged at the pharmacy 10 and delivered to the facility 100.

As shown in FIG. 1, the medicine management system 1 includes a management server 200, and manages the receipt status and the dosage status of the medicines delivered from the pharmacy 10 by a management server 200.

The pharmacy 10 is provided with a receipt computer 12, a packaging device 14, a one-dose-packaging audit support device 16, and the like. The receipt computer 12, the packaging device 14, and the one-dose-packaging audit support device 16 are communicably connected to one another. Further, the one-dose-packaging audit support device 16 is communicably connected to the management server 200 via a network 2 such as the Internet.

The facility 100 is provided with a portable terminal 102. At least one portable terminal 102 is provided in one facility 100. The portable terminal 102 is communicably connected to the management server 200 via the network 2.

Only one pharmacy 10 and only one facility 100 are shown in FIG. 1, but there may be a plurality of pharmacies 10 and a plurality of facilities 100.

[Devices Equipped in Pharmacy]

[Receipt Computer]

A receipt computer 12 is a computer for creating a receipt (medical fee bill). Information described in a prescription (prescription information) is input to the receipt computer 12. The prescription information includes information on a patient, information on prescribed medicines, information on a hospital which has provided a prescription, and the like. The information on the patient includes information such as the name, age and gender of the patient, an admitting facility, etc. The information on the medicines includes information on the names of the medicines, the amounts of the medicines, the usage of the medicines (dosage timings), doses of medicine, an instruction for one-dose-packaging, and the like. The information on the hospital includes information on the name of the hospital, the mane of a doctor, the date of issue of the prescription and the like. In the foregoing description, "patient" is synonymous with "facility resident" and "person who takes medicines".

The prescription information (prescription data) input to the receipt computer 12 is output to the packaging device 14 and the one-dose-packaging audit support device 16.

[Packaging Device]

The packaging device 14 one-dose-packages medicines to be prescribed to a patient based on prescription information acquired from the receipt computer 12. Since the packaging device itself has a known configuration, a detailed description thereof is omitted. The one-dose-packaged medicines (packaged medicines) are discharged from the packaging device 14 while respective packaging bags are connected to one another in a band shape (a state of a so-called packaged article) (see FIG. 3). Note that the one-dose-packaging processing is performed for each patient.

[One-Dose-Packaging Audit Support Device]

The one-dose-packaging audit support device 16 is a device for supporting an audit work to be performed on one-dose-packaged medicines by a pharmacist. The audit work is a work in which a pharmacist checks the types and numbers of dispensed medicines when delivering the medicines to a patient, thereby ensuring accuracy and securing safety. The one-dose-packaging audit support device 16 of the embodiment reads engraved stamps and characters on tablets, colors and shapes of capsules or the like for each packaging bag, and automatically performs the processing of determining the name and number or quantity of each medicine for each packaging bag.

Figure 2:
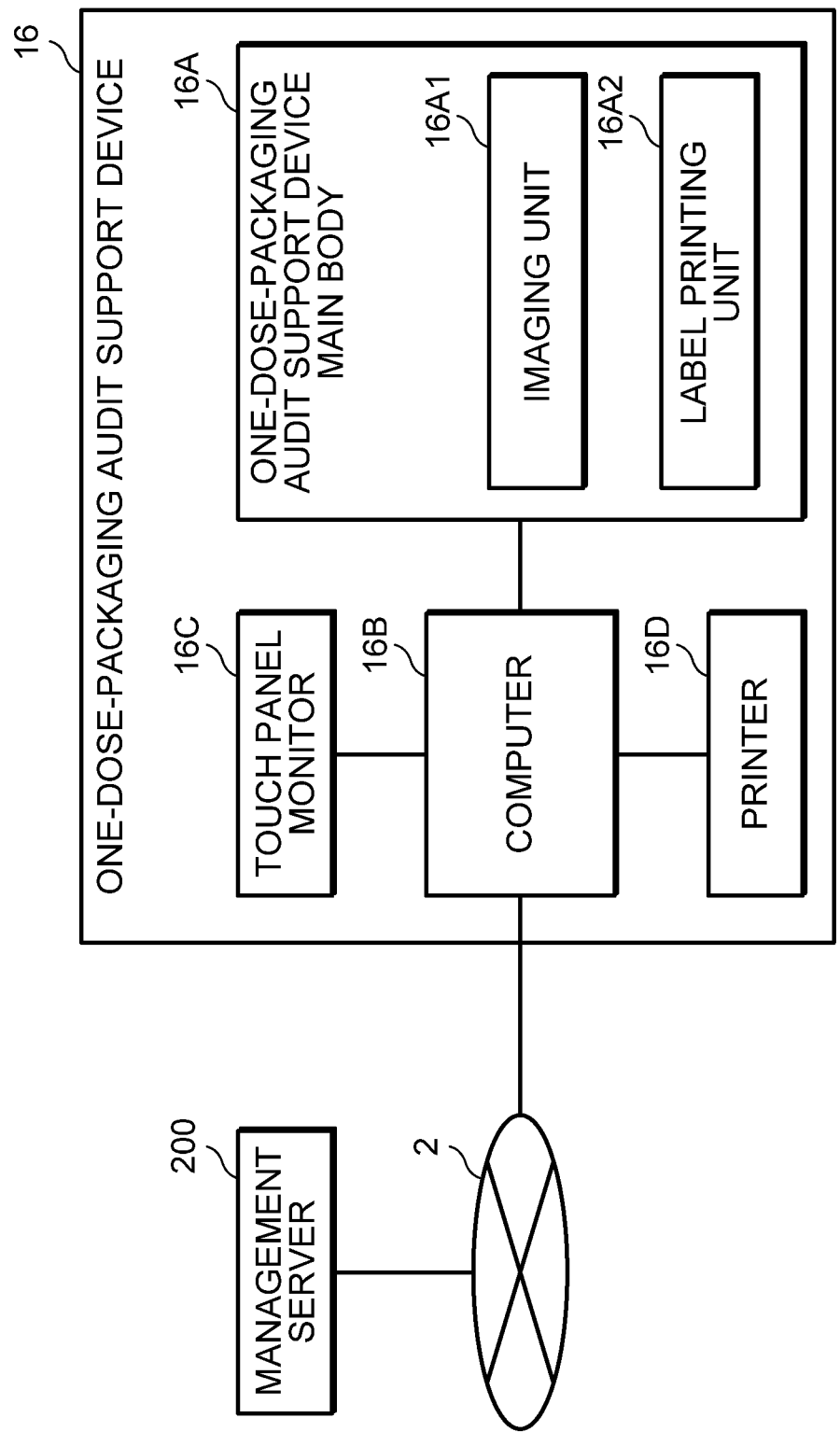
FIG. 2 is a block diagram showing a schematic configuration of a one-dose-packaging audit support device.

FIG. 2 is a block diagram showing a schematic configuration of the one-dose-packaging audit support device.

The one-dose-packaging audit support device 16 is mainly composed of a one-dose-packaging audit support device main body 16A, a computer 16B, a touch panel monitor 16C, a printer 16D, and the like.

[One-Dose-Packaging Audit Support Device Main Body]

The one-dose-packaging audit support device main body 16A takes in a string of packaged medicines in which packaging bags are connected to one another in a band shape, and captures an image of each packaging bag individually. Further, for a string of packaged medicines for which an audit has been completed, labels having prescribed items printed thereon are attached onto the respective packaging bags, and then the string of packaged medicines are discharged. Therefore, the one-dose-packaging audit support device main body 16A is provided with an imaging unit 16A1 and a label printing unit 16A2.

The imaging unit 16A1 individually captures images of the string of packaged medicines bag by bag. At this time, in order to accurately grasp the shapes, engraved stamps, etc. of medicines, images are captured from both sides of each bag. In other words, images are captured from the front and back sides. The captured images are output to the computer 16B.

The label printing unit 16A2 prints a predetermined item on a label, and attaches the label onto each packaging bag. The printing method is not particularly limited, and a heat-sensitive method for printing on dedicated heat-sensitive paper, a thermal transfer method using an ink ribbon, an inkjet method, or the like can be adopted.

Figure 3:
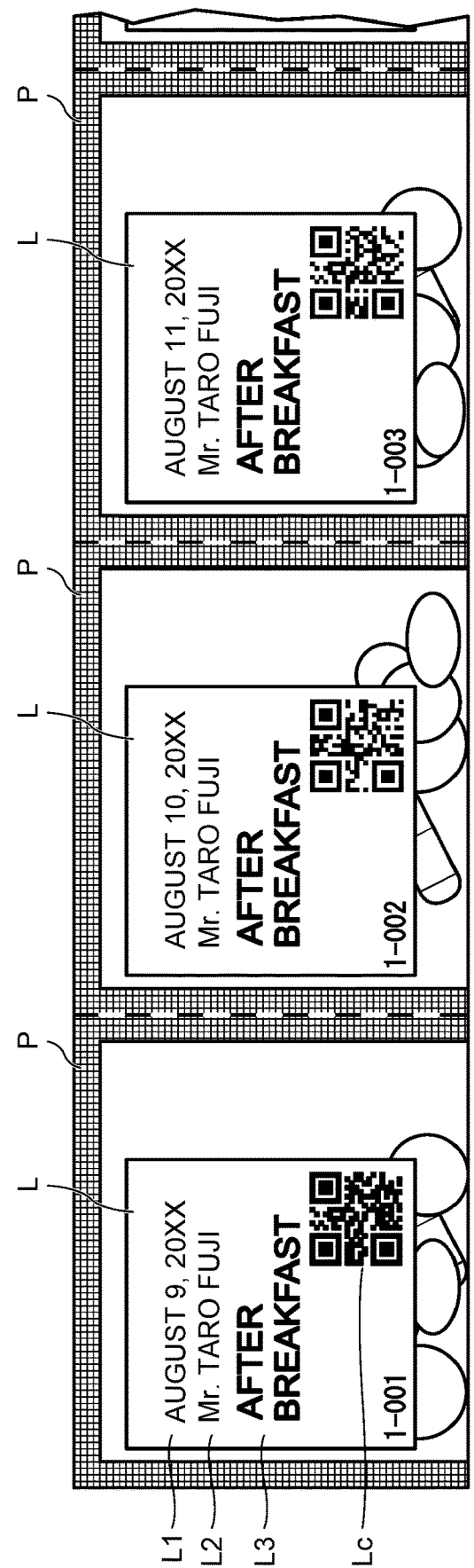
FIG. 3 is a diagram showing an example of labels and one-dose-packaging bags to which the labels are affixed.

FIG. 3 is a diagram showing an example of labels and packaging bags to which the labels are attached.

As shown in FIG. 3, a label L is individually attached to each packaging bag P. Information on a scheduled dosage date L1, a patient's name (Taro Fuji) L2, a dosage timing L3 and the like is printed on the label L as information indicating a dispensing content. Further, a two-dimensional code Lc is printed on the label L. This two-dimensional code Lc is obtained by encoding unique medicine identification information given to each bag. Here, FIG. 3 shows an example in which the medicine identification information is encoded with a QR code (registered trademark).

For example, a GS1 identification code (an international standard identification code defined by General Specifications One (GS1)) can be adopted for the medicine identification information. The GS1 identification code includes a global trade item number (GTIN) code, a global location number (GLN) code, a global individual asset identifier (GIAI) code, a serial shipping container code (SSCC) code, a global returnable asset identifier (GRAI) code, a global service relation number (GSRN) code, a global document type Identifier (GDTI) code, a global coupon number (GCN) code, and the like, and the GSRN code and the GIAI code are particularly preferable.

The GSRN code is an identification code for managing service providers and users, and it includes a combination of a 9-digit GS1 business operator code, an 8-digit service provider or user code, a 10-digit extended region, and a 15-digit unique code that can be arbitrarily defined. Therefore, for example, a serial number (manufacturing number, individual identification number) of a one-dose-packaging audit support device is assigned to a service provider or user code of a GSRN code, and a serial number of the number of packaged medicines audited by the one-dose-packaging audit support device or a time stamp thereof is assigned to an extended region or a unique code, whereby the GSRN code can be used as unique medicine identification information.

The GIAI code is an identification code for managing the assets of a company, and it is a code of 30 digits at maximum which includes a 9-digit GS1 business operator code and a length-variable asset number of 1 to 21-digits. Therefore, a serial number of a one-dose-packaging audit support device and a serial number of the number of packaged medicines audited by using the one-dose-packaging audit support device or a time stamp thereof is assigned to the 21-digit asset number of the GIAI code, whereby the GIAI code can be used as unique medicine identification information.

The label printing unit 16A2 acquires print data on the label L from the computer 16B, and prints the print data on the label L. Further, the label printing unit 16A2 attaches the printed label L to each packaging bag P.

[Computer]

The computer 16B integrally controls the overall operation of the one-dose-packaging audit support device 16. The computer 16B includes, for example, a personal computer containing a central processing unit (CPU), a read only memory (ROM), a random access memory (RAM), a hard disk drive (HDD), a communication interface, and the like. Various programs and various data to be executed by the CPU are stored in the HDD.

Figure 4:
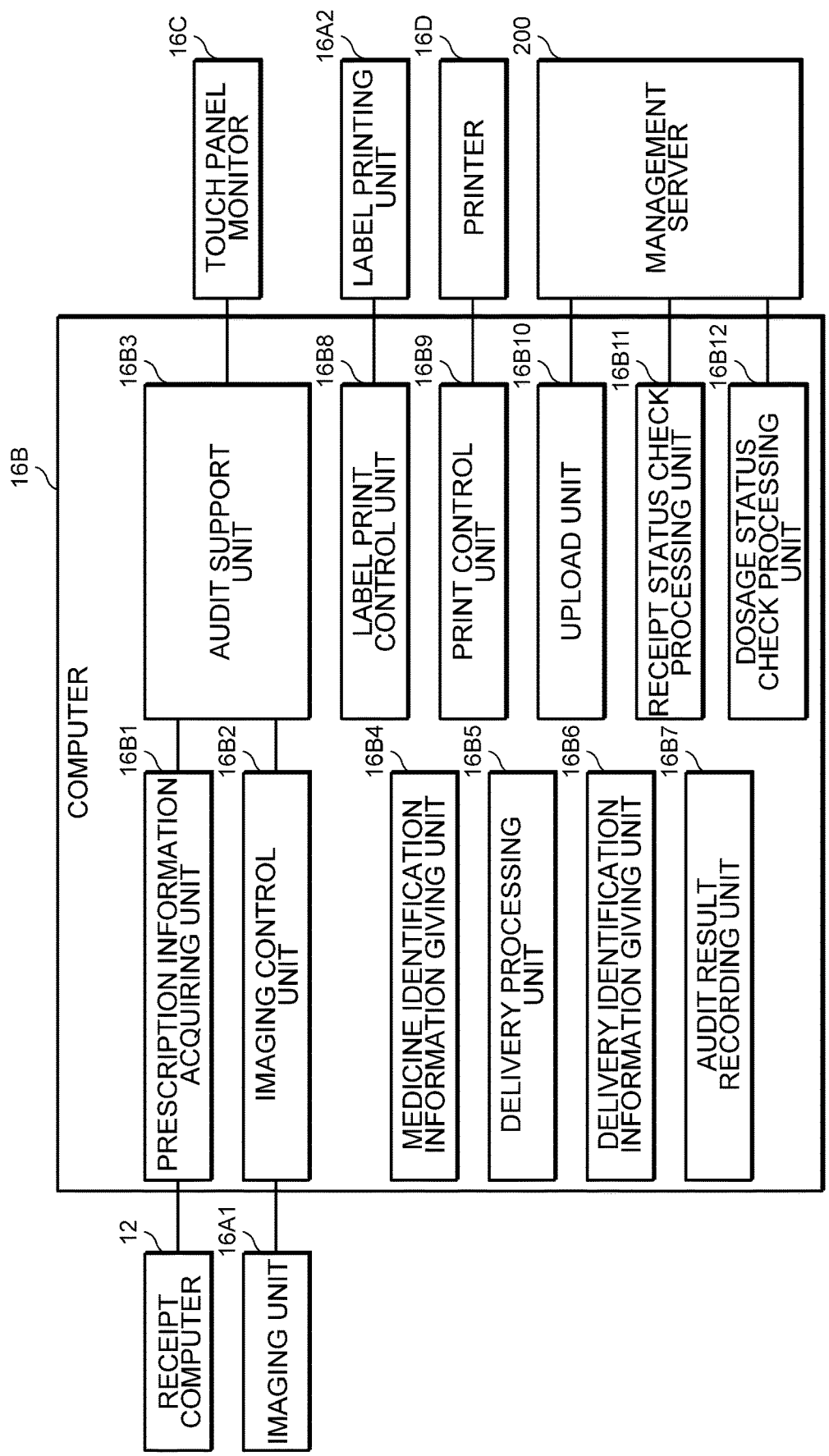
FIG. 4 is a block diagram of functions implemented by a computer of the one-dose-packaging audit support device.

FIG. 4 is a block diagram of functions to be implemented by the computer of the one-dose-packaging audit support device.

A computer 16B executes predetermined control programs to function as a prescription information acquiring unit 16B1, an imaging control unit 16B2, an audit support unit 16B3, a medicine identification information giving unit 16B4, a delivery processing unit 16B5, a delivery identification information giving unit 16B6, an audit result recording unit 16B7, a label print control unit 16B8, a print control unit 16B9, an upload unit 16B10, a receipt status check processing unit 16B11, a dosage status check processing unit 16B12, and the like.

The prescription information acquiring unit 16B1 acquires prescription information of a string of packaged medicines to be audited from the receipt computer 12.

The imaging control unit 16B2 controls the imaging unit 16A1 of the one-dose-packaging audit support device main body 16A to acquire images for audit support. In other words, the imaging control unit 16B2 acquires images which are obtained by imaging packaged medicines contained in each packaging bag from the front and back sides thereof, respectively.

The audit support unit 16B3 performs the processing of supporting an audit on the packaged medicines based on the images captured by the imaging unit 16A1 (the image captured from the front side of the packaging bag and the image captured from the back side of the packaging bag) and the prescription information. Specifically, the medicines contained in each bag are extracted from the captured images, and the shapes, dimensions, colors, characters, engraved stamps, etc. of the medicines are recognized and collated with the prescription information (so-called machine audit). Then, the collation result is displayed on the touch panel monitor 16C. The collation is performed, for example, by comparison with master images of the prescribed medicines. The master images are stored as a database in advance in HDD. Information on medicines and captured images (master images) of the medicines are recorded in association with each other in the database.

Figure 5:
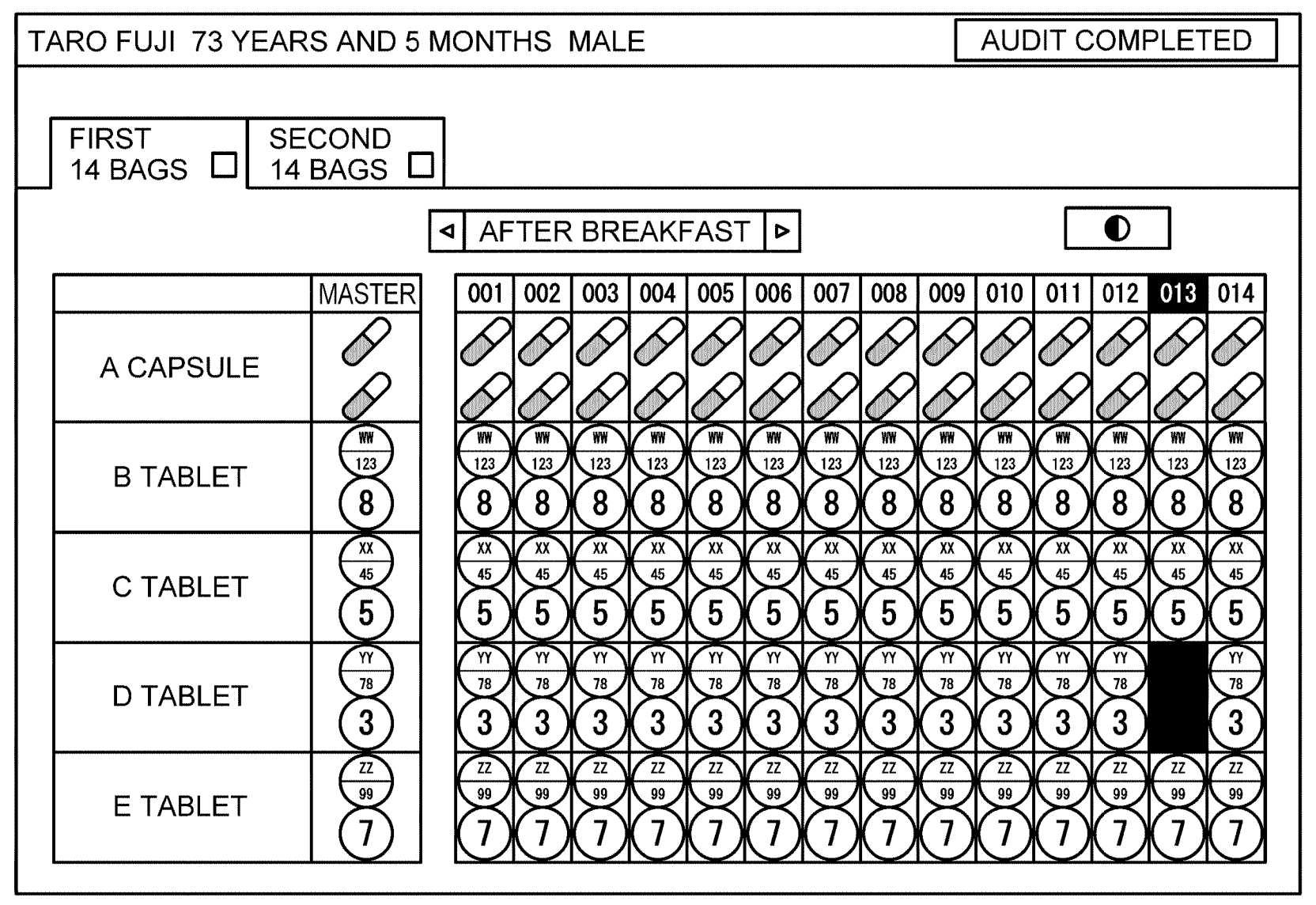

FIG. 5 is a diagram showing a display example of a collation result. FIG. 5 shows an example of a collation result for 14 bags, and illustrates a case where five medicines (A capsule, B tablet, C tablet, D tablet, E tablet) are contained in each bag.

As shown in FIG. 5, on a display screen of the collation result, the master information of the prescription is displayed, and collation results for respective bags are displayed as a list in the form of tiles. More specifically, the images (the image of the front side and the image of the back side) of the medicines extracted from each bag are displayed side by side in each column. At this time, the images are displayed while the directions of the engraved stamps or characters are aligned with one another. The medicines within each field are displayed to be arranged in the same alignment sequence as the medicines displayed in the field of the prescription master information. Further, master images for medicines are displayed on a medicine basis in the field of prescription master information. A pharmacist uses these master images to visually audit the medicines contained in each bag. In other words, the pharmacist determines whether or not each bag is correctly one-dose-packaged according to the prescription information.

Note that when a bag different from the prescription information is detected by the machine audit, the bag is displayed in a manner which enables the bag to be distinguished from the other bags. FIG. 5 shows an example when a thirteenth bag is different from the prescription information. In this case, the bag number (013) of the bag different from the prescription information is displayed in a form which is distinguishable from that of the other bags, and an image portion of a medicine (D tablet) different from the prescription information is displayed in a form which is distinguishable from those of the other bags. For example, the medicine is displayed with a background color different from that of the other bags.

When the audit by the pharmacist is completed, the pharmacist touches an "Audit Completed" button displayed on the screen, whereby the audit is completed.

The medicine identification information giving unit 16B4 gives unique medicine identification information to each bag as an audit target. As a result, unique medicine identification information is given to each bag of one-dose-packaged medicines on a bag basis.

The delivery processing unit 16B5 creates a list of medicines to be delivered to the same delivery destination on the same day (shipping-scheduled medicine list). For example, the delivery processing unit 16B5 displays, on the touch panel monitor 16C, a list of patients for which medicine audits have been performed, accepts selection of patients (facility residents) for which medicines will be delivered to the same delivery destination (facility) on the same day, and creates a shipping-scheduled medicine list. Note that when there are a plurality of facilities that respond to demands of prescriptions, it is preferable to accept selection of facilities and enable selection of patients to be accepted on a facility basis.

The shipping-scheduled medicine list is created based on the prescription information of a selected patient. Therefore, when medicines other than packaged medicines (for example, eye drops, liquid medicines, medicines for external use, etc.) are prescribed, these medicines are also listed in a shipping-scheduled medicine list.

The delivery identification information giving unit 16B6 gives unique delivery identification information to the shipping-scheduled medicine list created by the delivery processing unit 16B5. As a result, unique delivery identification information is given to medicines to be delivered from a pharmacy for each delivery. The delivery identification information is, for example, the name or ID of a facility as a delivery source, the name or ID of a facility as a delivery destination, a combination of the names or IDs of facilities as a delivery source and a delivery destination, a combination of the names or IDs of facilities as a delivery source and a delivery destination and a serial number or time stamp of delivery, a combination of a serial number of a one-dose-packaging audit support device and a serial number or time stamp of delivery, and the like.

The audit result recording unit 16B7 records an audit result in the HDD. At this time, the images used for the machine audit (captured images, and images of each medicine extracted for collation) are recorded on a bag basis. In addition, the medicine identification information given to each bag is recorded in association with the images. This makes it possible to access audit results from the medicine identification information. Further, delivery identification information is recorded in association with the medicine identification information. As a result, medicines which have been delivered at the same timing can be identified from the delivery identification information.

The label print control unit 16B8 controls label printing and attachment by the label printing unit 16A2. The label printing unit 16A2 acquires prescription information and medicine identification information to create print data for labels. Further, the label print control unit 168 controls the label printing unit 16A2 to print a predetermined item on a label based on the created print data (see FIG. 3). As described above, the item to be printed on the label includes a two-dimensional code Lc. The label print control unit 16B8 encodes the medicine identification information with a two-dimensional code and prints it on the label.

The print control unit 16B9 controls printing by the printer 16D. For example, the print control unit 16B9 prints a shipping-scheduled medicine list according to a print instruction from a user. At this time, the print control unit 16B9 prints the shipping-scheduled medicine list with the delivery identification information being added thereto. In the present embodiment, the delivery identification information is encoded with a two-dimensional code (for example, a QR code) and then printed. When medicines are delivered to a delivery destination, the printed shipping-scheduled medicine list is delivered with the medicines. A printed matter with a shipping-scheduled medicine list is an example of a delivery object to be delivered with medicines.

The upload unit 16B10 acquires the medicine identification information and the prescription information, and transmits the medicine identification information to the management server 200 with information extracted from the prescription information being associated with the medicine identification information. Further, the upload unit 16B10 acquires the delivery identification information, and transmits the delivery identification information to the management server 200 with the delivery identification information being associated with the medicine identification information. The upload unit 16B10 is an example of a medicine identification information transmitting unit, and an example of a delivery identification information transmitting unit.

The receipt status check processing unit 16B11 transmits a check request for the receipt status of medicines to the management server 200 in response to an instruction from the user. Further, the receipt status check processing unit 16B11 acquires information on the receipt status of medicines transmitted from the management server 200 in response to the check request, and displays a result on the touch panel monitor 16C. The instruction of the check request is given, for example, by calling a check screen of the receipt status of medicines. The check screen of the receipt status of medicines is called from a menu screen (also referred to as a home screen or a main screen). When the check screen of the receipt status of medicines is called, the delivery identification information of shipped medicines is displayed in the form of a list as a delivery history. Besides, the receipt status is displayed for each delivery identification information. The receipt status is displayed as, for example, "received" if the medicines have been received, and "unreceived" if the medicines have not been received. When the check screen of the receipt status is called, delivery identification information under an unreceived state is detected. Thereafter, a check request for the receipt status is made for the delivery of the detected delivery identification information. Specifically, the delivery identification information under the unreceived state is transmitted to the management server 200 together with the check request of the receipt status. The management server 200 refers to a management database to acquire the information on the receipt status of the corresponding delivery identification information, and returns the information to the receipt status check processing unit 16B11. The receipt status check processing unit 16B11 updates the item of the receipt status of each delivery identification information listed on the touch panel monitor 16C based on the returned information on the receipt status. In other words, if the medicine has been received, the item is changed to "received".

The dosage status check processing unit 16B12 transmits a check request for the dosage status of medicines to the management server 200 in response to an instruction from the user. In addition, the dosage status check processing unit 16B12 acquires information on the dosage status of medicines transmitted from the management server 200 in response to the check request, and displays a result on the touch panel monitor 16C. The instruction for the check request is performed, for example, on a check screen for the dosage status. The check screen for the dosage status is called from the menu screen. When the check screen for the dosage status is called, a list of facilities to which medicines have been delivered is displayed. When one facility is selected from the facilities whose list is displayed, a list of patients admitted to the selected facility is displayed. Further, when one patient is selected from the patients whose list is displayed, medicine identification information on medicines which have been delivered from a pharmacy to the patient is displayed in the form of a list as a dosage history of the patient. Besides, the dosage status is displayed for each medicine identification information. The dosage status is displayed as, for example, "taken" if the patient has already taken a medicine, and "untaken" if the patient has not yet taken a medicine. When the patient is selected, medicine identification information indicating a medicine-untaken state is detected. Then, a check request for the dosage status is made for medicines of the detected medicine identification information. Specifically, the medicine identification information indicating a medicine-untaken state is transmitted to the management server 200 together with the check request for the dosage status. The management server 200 refers to the management database to acquire information on the dosage status of the corresponding medicine identification information, and returns the information to the dosage status check processing unit 16B12. The dosage status check processing unit 16B12 updates the item of the dosage status of each medicine identification information displayed in the form of a list on the touch panel monitor 16C based on the returned information on the dosage status. In other words, if the medicine has been taken, the item is changed to "taken".

The computer 16B is an example of a third terminal in that it has a function of acquiring and displaying information on the receipt status and the dosage status of medicines from the management server 200. Since the computer 16B constitutes a one-dose-packaging audit support device 16, the one-dose-packaging audit support device 16 is also an example of the third terminal. In other words, in the medicine management system 1 of the present embodiment, the one-dose-packaging audit support device 16 also serves as the third terminal.

[Touch Panel Monitor]

The touch panel monitor 16C is connected to the computer 16B and functions as a display device and an input device of the computer 16B.

[Printer]

The printer 16D is connected to the computer 16B and prints on paper according to an instruction from the computer 16B. The printer 16D is an example of the printing unit. The printing method of the printer 16D is not particularly limited, and a heat-sensitive method, a thermal transfer method, an inkjet method, or the like can be adopted.

[Equipment Installed in Facilities]

[Portable Terminal]

The portable terminal 102 includes a portable computer having a communication function and a camera function. Specifically, it includes a smartphone, a tablet terminal, or the like, and is provided with a touch panel monitor that also serves as display means and input means. A user ID (Identification) is assigned to the portable terminal 102, and a user (a facility owing the portable terminal 102) is specified by the user ID. Note that when the facility 100 is provided with a plurality of portable terminals 102, a user ID is assigned to each of the portable terminals 102. Alternatively, a user ID common in the facility 100 (for example, an ID assigned to the facility (facility code or the like)) is assigned.

A predetermined control program is installed in the portable terminal 102, and various functions are implemented by executing the program.

Figure 6:
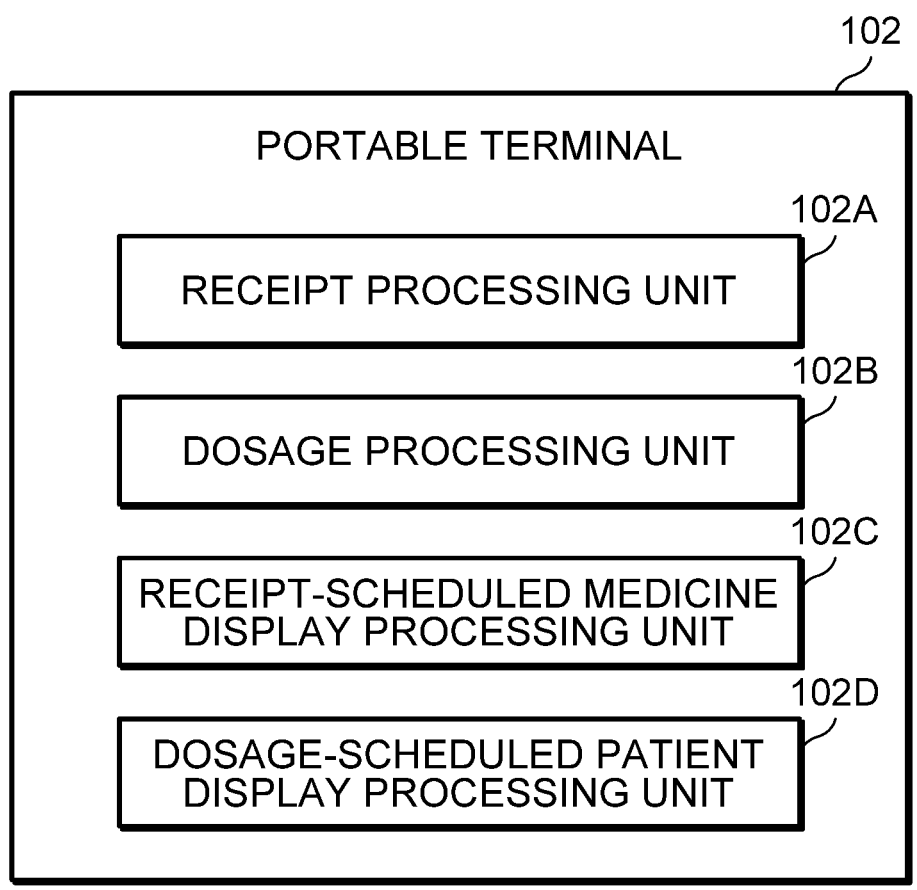
FIG. 6 is a block diagram of functions possessed by a portable terminal.

FIG. 6 is a block diagram of functions of the portable terminal.

As shown in FIG. 6, the portable terminal 102 functions as a receipt processing unit 102A, a dosage processing unit 102B, a receipt-scheduled medicine display processing unit 102C, a dosage-scheduled patient display processing unit 102D, and the like.

When medicines delivered from a pharmacy are received, the receipt processing unit 102A reads, by a camera, a two-dimensional code (two-dimensional code indicating delivery identification information) printed on a printed matter (a medium on which a shipping-scheduled medicine list is printed) delivered together with the medicines, and notifies the management server 200 of information indicating receipt. Specifically, the receipt processing unit 102A decodes the read-out two-dimensional code to acquire the delivery identification information, and notifies (transmits) the information as information indicating receipt to the management server 200. As described later, the management server 200 determines the success or failure in delivery based on transmitted delivery identification information and the user ID of the portable terminal 102 which has transmitted the delivery identification information. In other words, it is determined whether or not the receipt is a receipt at a designated delivery destination. Then, the management server 200 transmits the determination result to the portable terminal 102. The receipt processing unit 102A displays the determination result on a monitor (touch panel monitor) which is a display unit.

The dosage processing unit 102B reads a two-dimensional code (two-dimensional code indicating medicine identification information) affixed to a packaging bag by a camera when a patient takes a medicine, and notifies the management server 200 of information indicating the dosage of the medicine. Specifically, the dosage processing unit 102B decodes the read two-dimensional code to acquire the medicine identification information, and notifies (transmits) the acquired medicine identification information as information indicating the dosage to the management server 200. When reading the two-dimensional code, the dosage processing unit 102B identifies the patient and reads the two-dimensional code. The dosage processing unit 102B notifies the management server 200 of the medicine identification information together with information on the identified patient. As described later, the management server 200 determines the success or failure in medicine dispensing based on the transmitted medicine identification information and the information on the patient. Then, the dosage processing unit 102B transmits the determination result to the portable terminal 102. The dosage processing unit 102B displays the determination result on the monitor.

The receipt-scheduled medicine display processing unit 102C requests the management server 200 to check a receipt-scheduled medicine (a medicine which is scheduled to be delivered from a pharmacy and received) in response to an instruction from a user. In addition, the receipt-scheduled medicine display processing unit 102C receives information (medicine identification information and information of a medicine scheduled to be delivered from the pharmacy) sent from the management server 200 in response to the check request, and displays the information in a predetermined format on the monitor.

The dosage-scheduled patient display processing unit 102D requests the management server 200 to check a dosage-scheduled patient (a patient who is scheduled to take a medicine) in response to an instruction from the user. In addition, the dosage-scheduled patient display processing unit 102D receives information (information on a patient who is scheduled to take a medicine) sent from the management server 200 in response to the check request, and displays the information in a predetermined format on the monitor.

In the medicine management system 1 of the present embodiment, the portable terminal 102 is an example of a first terminal and a second terminal. In other words, in the medicine management system 1 of the present embodiment, the portable terminal 102 also serves as the first terminal and the second terminal.

[Management Server]

The management server 200 includes a computer having a communication function, and implements various functions by executing predetermined control programs.

Figure 7:
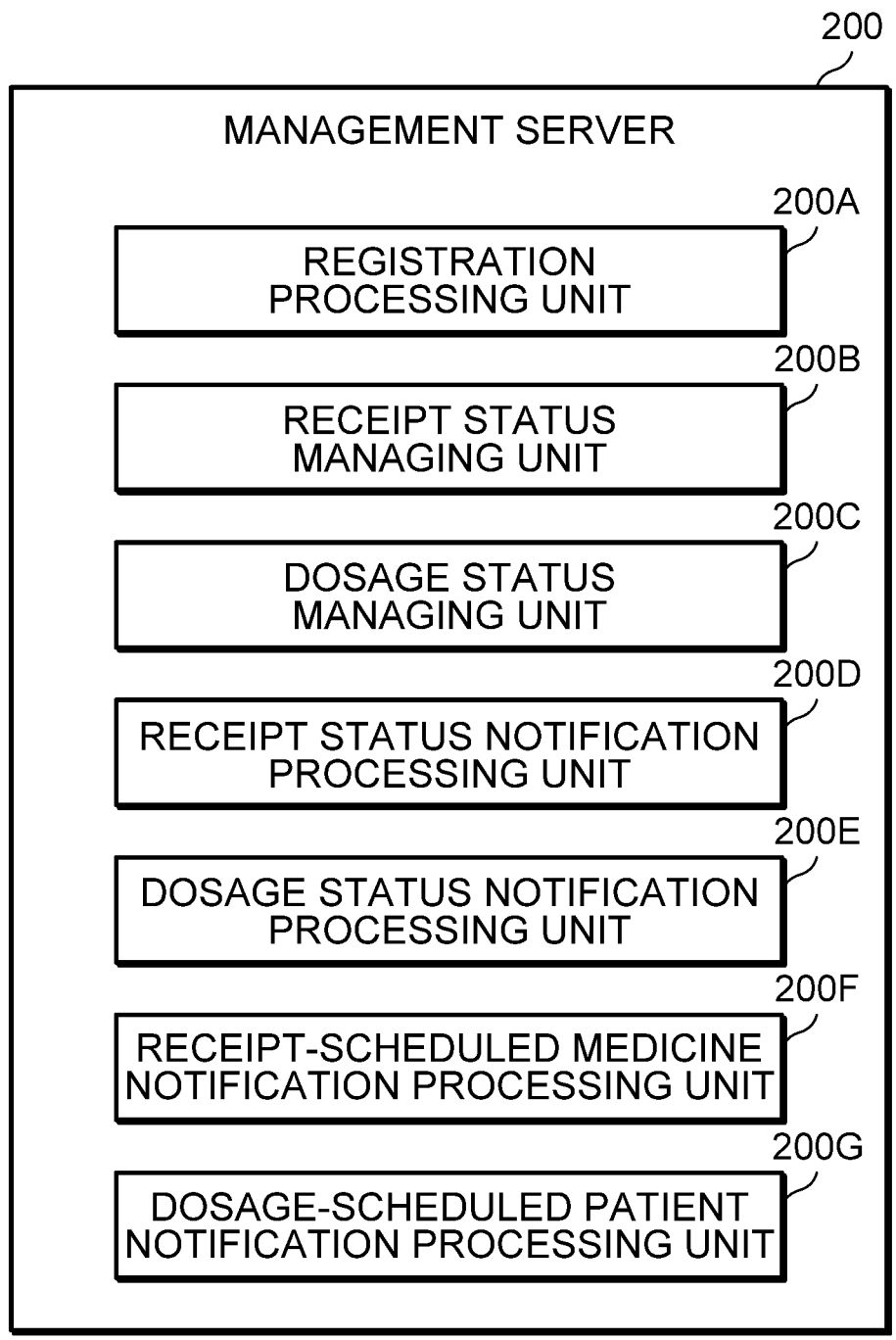
FIG. 7 is a block diagram of functions possessed by a management server.

FIG. 7 is a block diagram of the functions of the management server.

As shown in FIG. 7, the management server 200 functions as a registration processing unit 200A, a receipt status managing unit 200B, a dosage status managing unit 200C, a receipt status notification processing unit 200D, a dosage status notification processing unit 200E, a receipt-scheduled medicine notification processing unit 200F, a dosage-scheduled patient notification processing unit 200G and the like.

When the registration processing unit 200A receives the medicine identification information, the delivery identification information, and the information extracted from the prescription information from the one-dose-packaging audit support device 16, the registration processing unit 200A registers the information in the management database.

FIG. 8 is a diagram showing an example of the management database.

Here, FIG. 8 shows an example in a case where the name of each patient (patient name), the age of the patient, the gender of the patient, the name of a facility to which the patient is admitted (the name of an admitting facility), the user ID of a portable terminal provided in the facility 100 to which the patient is admitted, delivery identification information, medicine identification information, the names of one-dose-packaged medicines (medicine names), a dosage timing, a receipt status, and a dosage status are registered.

The facility to which the patient is admitted is identical to a facility to which medicines are delivered. Therefore, the name of the admitting facility is identical to the name of a delivery destination.

The user ID of the portable terminal is registered by referring to a user ID database. The facility name and the user ID of the portable terminal 102 provided in the facility 100 are recorded in association with each other in the user ID database. Therefore, once the admitting facility name is determined, the user ID of the portable terminal is uniquely determined. Note that when a plurality of portable terminals 102 are provided in the facility 100 and user IDs are individually assigned to the respective portable terminals 102, the user IDs of all the portable terminals 102 to be used in the facility 100 are registered. On the other hand, when a common user ID is used in one facility 100, the commonly used user ID is registered.

The receipt status is an item for indicating the receipt status of delivery of medicines. The receipt status is set to "unreceived" at the time of registration, and set to "received" when receipt is confirmed.

The dosage status is an item for indicating the status of taking a medicine. The dosage status is set to "untaken" at the time of registration, and set to "taken" when the dosage is confirmed.

The information necessary for registering this management database is extracted from the prescription information and transmitted from the one-dose-packaging audit support device 16 to the management server 200.

The receipt status managing unit 200B manages the receipt status of medicines delivered from the pharmacy 10 to the facility 100. The receipt status managing unit 200B determines the success or failure in delivery based on the delivery identification information and the user ID of the portable terminal 102 transmitted from the portable terminal 102 of the delivery destination facility 100, and transmits the result to the portable terminal 102. Further, when the medicine has been delivered to a correct delivery destination, the receipt status managing unit 200B updates the item of the receipt status in the management database. In other words, the item is change from an "unreceived" state to a "received" state.

The success or failure in delivery is determined based on delivery identification information and the user ID of a portable terminal 102 that has transmitted the delivery identification information. When the user ID of the portable terminal 102 that has transmitted the delivery identification information matches the user ID of a portable terminal associated with the delivery period information, the delivery is determined to be correct. On the other hand, when both the user IDs do not match each other, the delivery is determined to be incorrect.

The dosage status managing unit 200C manages the dosage status of medicines. The dosage status managing unit 200C determines the success or failure in medicine dispensing based on the medicine identification information and the patient information (for example, patient name, date of birth, gender) transmitted from the portable terminal 102 of the facility 100 of the delivery destination, and transmits the result to the portable terminal 102. When the medicine is dispensed correctly, the dosage status managing unit 200C updates the item of the dosage status in the management database. In other words, the item is changed to the "untaken" state to the "taken" state.

The success or failure in medicine dispensing is determined by collating the received medicine identification information and patient information with the information recorded in the management database. In other words, based on the received medicine identification information, the patient information registered in the management database is read out, and it is determined whether or not the read-out information matches the received patient information. If they match each other, the medicine dispensing is determined to be correct, and if they do not match each other, the medicine dispensing is determined to be incorrect.

The receipt status notification processing unit 200D transmits information on the receipt status of the medicine in response to the check request for the receipt status from the one-dose-packaging audit support device 16. As described above, the delivery identification information is identified and the check request for the delivery status is made from the one-dose-packaging audit support device 16. The receipt status notification processing unit 200D refers to the management database to read out the information of the receipt status of the delivery identification information transmitted from the one-dose-packaging audit support device 16, and transmits the read-out information to the one-dose-packaging audit support device 16.

The dosage status notification processing unit 200E transmits information on the receipt status of medicines in response to a check request for the dosage status from the one-dose-packaging audit support device 16. As described above, the medicine identification information is identified and the check request for the dosage status is made from the one-dose-packaging audit support device 16. The receipt status notification processing unit 200D refers to the management database to read out information on the dosage status of the medicine identification information transmitted from the one-dose-packaging audit support device 16, and transmits the read-out information to the one-dose-packaging audit support device 16.

The receipt-scheduled medicine notification processing unit 200F transmits information on a medicine scheduled to be delivered from a pharmacy and delivery identification information in response to a check request for a receipt-scheduled medicine from the portable terminal 102. When receiving the check request for the receipt-scheduled medicine from the portable terminal 102, the receipt-scheduled medicine notification processing unit 200F collects information on medicines scheduled to be delivered from the pharmacy and delivery identification information from the management database based on the user ID of the portable terminal 102, and transmits the collected information to the portable terminal 102.

The dosage-scheduled patient notification processing unit 200G transmits information on dosage-scheduled patients in response to a check request for dosage-scheduled patients from the portable terminal 102. When receiving the check request of the dosage-scheduled patients from the portable terminal 102, the receipt-scheduled medicine notification processing unit 200F collects the information on the dosage-scheduled patients from the management database based on the user ID of the portable terminal 102, and transmits the collected information to the portable terminal 102.

[Operation of Medicine Management System]

[Processing Until Medicine Delivery at Pharmacy]

Figure 9:
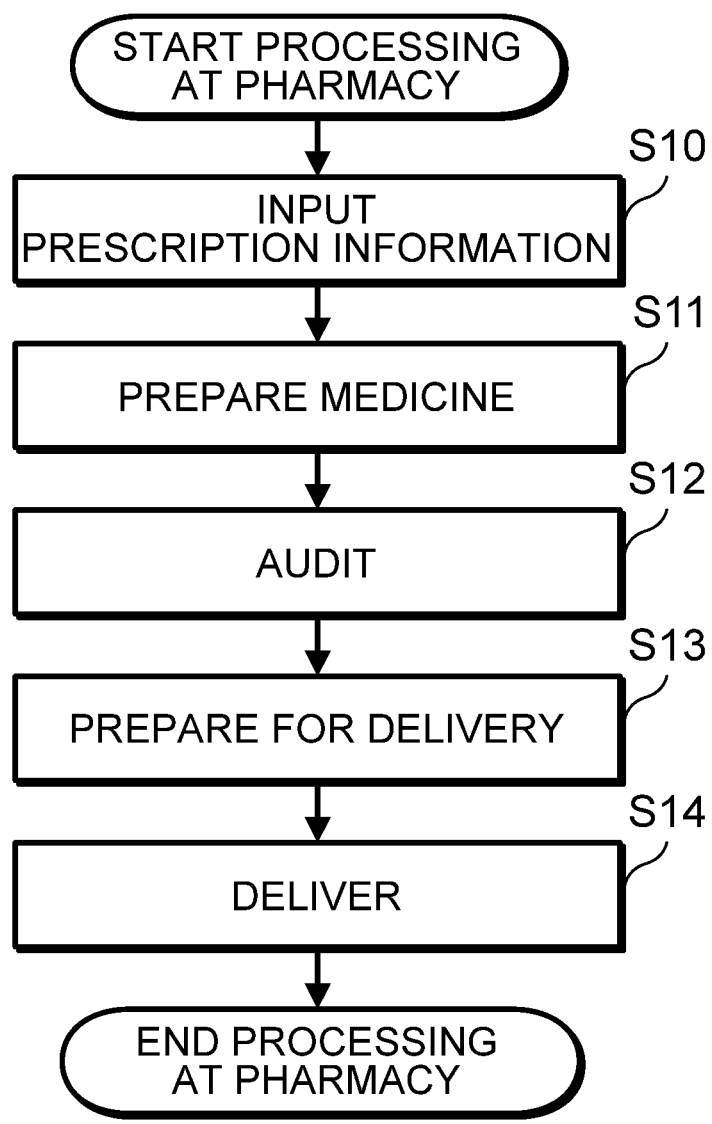
FIG. 9 is a flowchart showing the procedure of processing to be performed at a pharmacy before medicines have been delivered.

FIG. 9 is a flowchart showing the procedure of processing to be performed at a pharmacy until medicines have been delivered.

First, prescription information is input to the receipt computer 12 based on an issued prescription (step S10). The prescription information input to the receipt computer 12 is output to the packaging device 14 and the one-dose-packaging audit support device 16.

Thereafter, medicines are prepared based on the prescription information (step S11). At this time, when one-dose-packaging is instructed, the one-dose-packaging processing is performed. The one-dose-packaging is performed by using the packaging device 14. The packaging device 14 performs the one-dose-packaging on medicines based on the prescription information acquired from the receipt computer 12.

Next, the prepared medicines are audited (step S12). At this time, the one-dose-packaged medicines (packaged medicines) are audited by using the one-dose-packaging audit support device 16.

Figure 10:
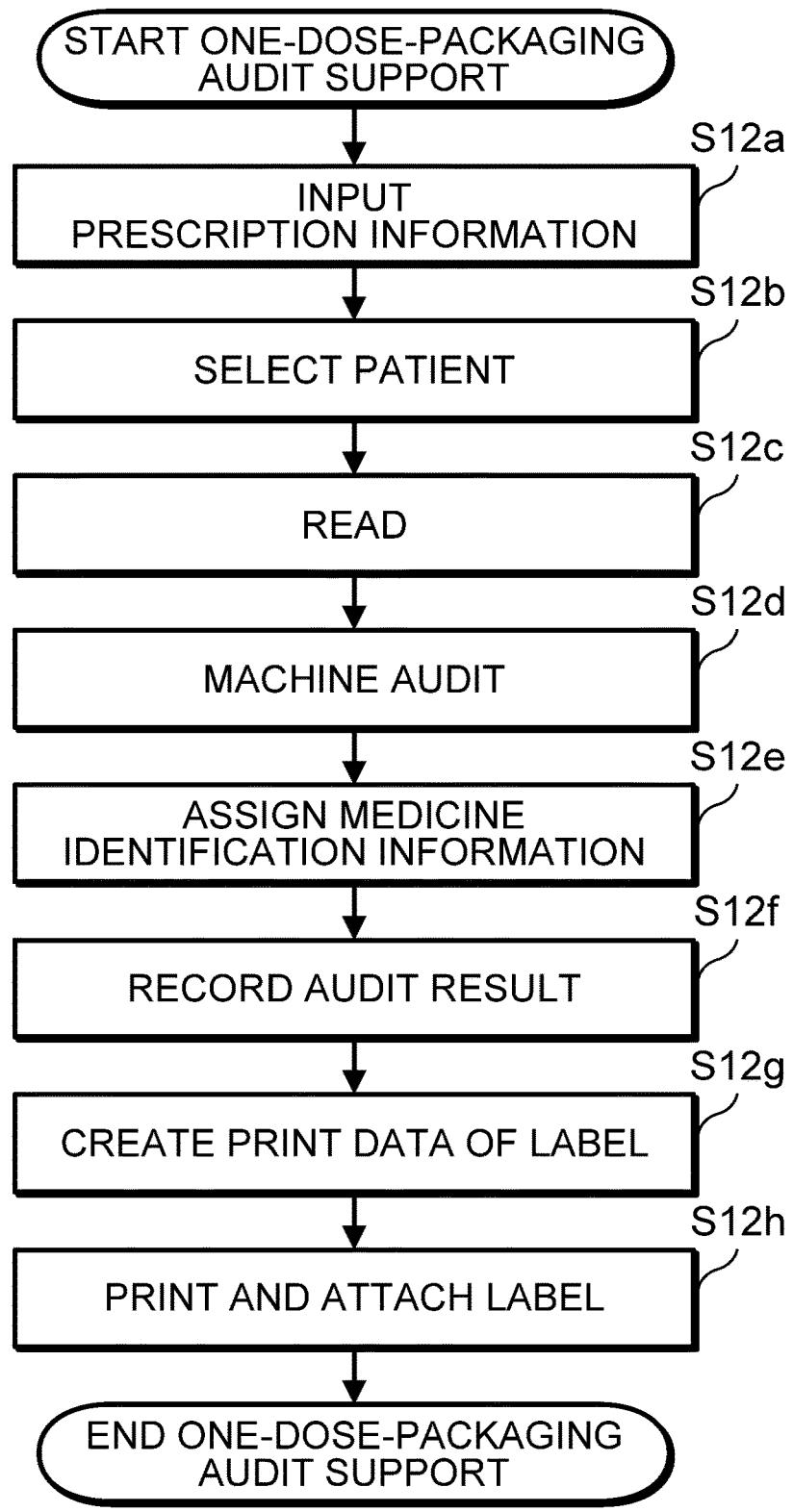
FIG. 10 is a flowchart showing the procedure of processing when an audit is performed by using the one-dose-packaging audit support device.

FIG. 10 is a flowchart showing the procedure of processing in the case of the audit using the one-dose-packaging audit support device.

First, the prescription information is input to the one-dose-packaging audit support device 16 (step S12a). The prescription information is acquired from the receipt computer 12 and input to the one-dose-packaging audit support device 16.

Next, a patient to be subjected to machine audit is selected (step S12b). The selection of a patient is performed by using the touch panel monitor 16C. A list of patients for which prescription information has been input is displayed on the touch panel monitor 16C. The user touches and selects a patient to be subjected to machine audit. When the patient is selected, master information of medicines prescribed for the patient is displayed on the touch panel monitor 16C (see FIG. 5).

Next, the one-dose-packaged medicines are read (step S12c). In other words, the one-dose-packaged medicines are set in the one-dose-packaging audit support device main body 16A, and imaged bag by bag.

When the imaging of all the packages is completed, the machine audit is performed based on the captured images and the prescription information (step S12d). In other words, the medicines contained in each bag are recognized by image processing, and collated with the prescription information. Then, the collation result is displayed on the touch panel monitor 16C (see FIG. 5). A pharmacist audits the medicines in each bag by using the collation result displayed on the touch panel monitor 16C.

When the audit is completed, medicine identification information is given to each bag (step S12e), and audit results are recorded in HDD (step S12f). The audit result is recorded for each bag, and recorded in association with the medicine identification information. In addition, the images used for the machine audit are also recorded in the audit results.

When the audit is completed, print data for labels are generated (step S12g). The print data for labels are generated based on the prescription information and the medicine identification information. The labels are printed based on the generated print data, and a label is attached onto each bag and discharged (step S12h).

The audit work using the one-dose-packaging audit support device 16 is completed in the above series of steps. When the audit on medicines for all patients admitted to the same facility 100 is completed, preparation for delivery is performed (step S13).

Figure 11:
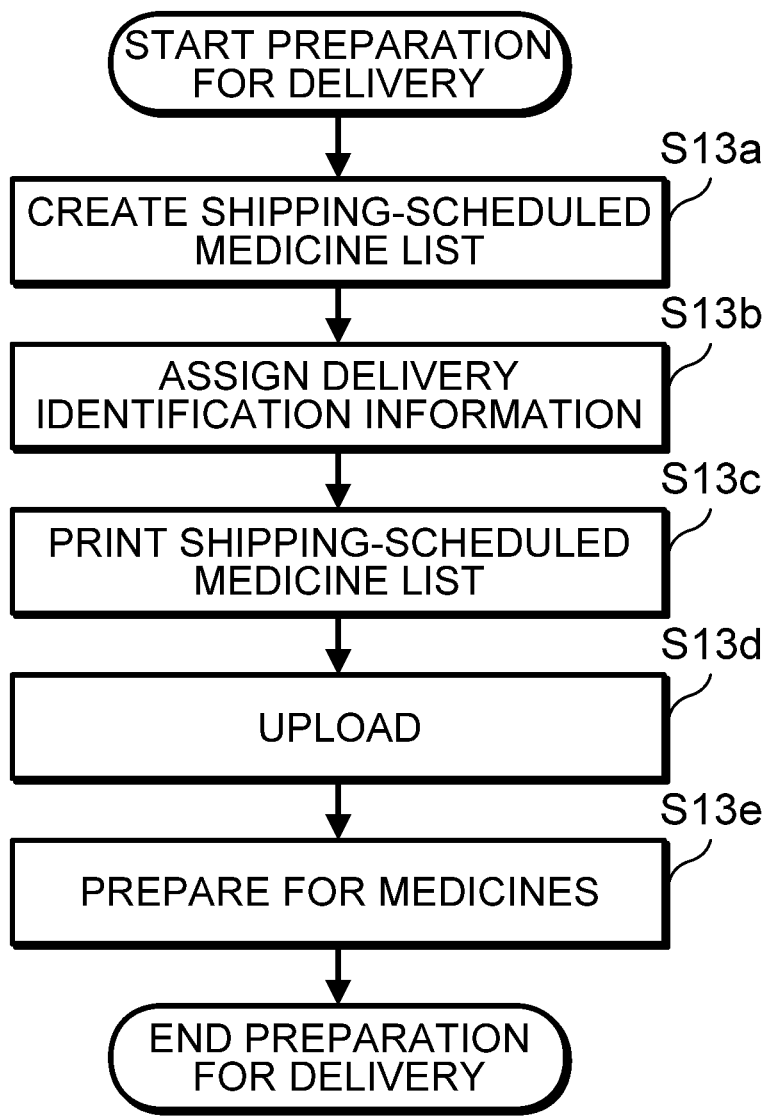
FIG. 11 is a flowchart showing the procedure of delivery preparation.

FIG. 11 is a flowchart showing the procedure of the preparation for delivery.

First, a shipping-scheduled medicine list is created (step S13a). The shipping-scheduled medicine list is a list of medicines which will be delivered to the same delivery destination (facility) on the same day. When a user instructs the one-dose-packaging audit support device 16 to create a shipping-scheduled medicine list, a list of patients for which audit has been performed on medicines is displayed on the touch panel monitor 16C. The instruction for creating the shipping-scheduled medicine list is performed, for example, by selecting an item of "create shipping-scheduled medicine list" from the menu screen. When there are a plurality of facilities that respond to demands of prescriptions, a facility is selected therefrom, and a list of patients in the selected facility is displayed. The information displayed in the form of a list includes information on ages, genders, admitting facility names, etc. of patients as well as the names of the patients. The user touches and selects a patient for which medicines will be delivered to the same delivery destination (facility) on the same day. When the selection is complete, a shipping-scheduled medicine list is created based on prescribing information for the selected patient.

The created shipping-scheduled medicine list is displayed on the touch panel monitor 16C. The user checks the display on the touch panel monitor 16C.

When the shipping-scheduled medicine list has been created, delivery identification information is created and added to the list (step S13b). The delivery identification information added to the shipping-scheduled medicine list is recorded in HDD in association with the medicine identification information of each medicine listed in the shipping-scheduled medicine list. Therefore, in the one-dose-packaging audit support device 16, the shipping-scheduled medicine list can be restored based on the delivery identification information.

A print button is displayed together with the created shipping-scheduled medicine lists on the touch panel monitor 16C. After checking the content of the list, the user touches the print button to instruct printing of the list. When printing is instructed, the shipping-scheduled medicine list is printed by the printer 16D (step S13c). A two-dimensional code obtained by encoding the delivery identification information is also printed on a printed matter of the list.

Further, an upload button is displayed together with the created shipping-scheduled medicine list on the touch panel monitor 16C. After checking the content of the list, the user touches the upload button to instruct upload of information. When upload is instructed, predetermined information is uploaded to the management server 200 (step S13d). Specifically, in addition to the medicine identification information of medicines (packaged medicines) listed in the shipping-scheduled medicine list, the information extracted from the prescription information and the delivery identification information are uploaded. The information extracted from the prescription information and the delivery identification information are uploaded in association with the medicine identification information. The information extracted from the prescription information includes information such as the names of the patients, the ages of the patients, the genders of the patients, the admitting facility, the names of medicines, and the dosage timings.

After the upload, the user prepares medicines to be delivered to the facility 100 based on the printed shipping-scheduled medicine list (step S13e). In other words, the user collects and arranges in a lump the medicines to be delivered to the same facility 100 on the same day and prepares for delivery.

The preparation for delivery is completed in the above series of processing. Thereafter, the medicines are delivered (step S14). When delivering the medicines, a printed matter on which the shipping-scheduled medicine list is printed is delivered together.

[Registration Process in Management Server]

The management server 200 receives information uploaded from the one-dose-packaging audit support device 16 and registers the uploaded information in the management database (see FIG. 8).

Further, the management server 200 accepts the registration of the user ID from the portable terminal 102 used in the facility 100, and registers the user ID in the user ID database. In the user ID database, the facility names and the user IDs are recorded in association with each other. The user ID database is referred to when information on the user ID is registered in the management database.

[Processing of Acquiring Receipt-Scheduled Medicine Information at Facility]

In the facility 100, information on receipt-scheduled medicines can be acquired in advance by using the portable terminal 102. When acquiring the information on the receipt-scheduled medicines, the user requests the management server 200 to check the receipt-scheduled medicines via the portable terminal 102. In this case, the user calls an execution screen for a check request for receipt-scheduled medicines, and instructs execution of the check request for receipt-scheduled medicines. When the execution of the check request for receipt-scheduled medicines is instructed, the check request for receipt-scheduled medicines is transmitted from the portable terminal 102 to the management server 200, and the information of the user ID is transmitted.

When the management server 200 receives the check request for receipt-scheduled medicines from the portable terminal 102, the management server 200 collects information on receipt-scheduled medicines and delivery identification information from the management database based on the user ID of the portable terminal 102, and transmits the collected information to the portable terminal 102. The portable terminal 102 displays the acquired delivery identification information and the information on the medicines in a predetermined format (for example, in the form of a list) on the monitor. The user views this display on the monitor to check the receipt-scheduled medicines.

[Medicine Receipt Processing at Facilities]

The medicine receipt processing is performed by reading a two-dimensional code printed on a printed matter (an article on which a shipping-schedule medicine list is printed) delivered together with medicines by the portable terminal 102 of the facility 100. The reading is performed by switching the portable terminal 102 to a two-dimensional code reading mode.

When the two-dimensional code printed on the printed matter is read out by the portable terminal 102, the read-out two-dimensional code is decoded to acquire delivery identification information. The portable terminal 102 transmits the acquired delivery identification information together with the user ID to the management server 200.

Upon receiving the delivery identification information and the user ID, the management server 200 refers to the management database and determines the success or failure in delivery. In other words, the management server 200 determines whether or not the received delivery identification information and the user ID match information registered in the management database. If the received delivery identification information and the user ID match the registered information, it is determined that medicines have been delivered correctly, and if the received delivery identification information and the user ID do not match the registered information, it is determined that the medicines have not been delivered correctly. This determination result is transmitted to the portable terminal 102. The portable terminal 102 displays the determination result transmitted from the management server 200 on the monitor. The user checks the success or failure in delivery by watching the display on this monitor. If the medicines have been delivered correctly, the user receives the delivered medicines.

Further, when the management server 200 determines that the medicines have been delivered to a correct delivery destination, the management server 200 updates the item of the receipt status of the management database. In other words, the management server 200 changes the item of the receipt status from the "unreceived" state to the "received" state.

[Processing of Acquiring Dosage-Scheduled Patient Information at Facilities]

At the facility 100, information on patients who are scheduled to take medicines (medicine takers) can be acquired by using the portable terminal 102. When acquiring information on dosage-scheduled patients, the user makes a request for checking dosage-scheduled patients to the management server 200 via the portable terminal 102. In this case, the user calls the execution screen for the check request for dosage-scheduled patients and instructs the execution of the check request for the dosage-scheduled patients. When the execution of the check request for the dosage-scheduled patients is instructed, the check request for the dosage-scheduled patients is transmitted from the portable terminal 102 to the management server 200, and the information of the user ID is also transmitted.

When receiving the check request for the dosage-scheduled patients from the portable terminal 102, the management server 200 collects information on the dosage-scheduled patients from the management database based on the user ID of the portable terminal 102, and transmits the information to the portable terminal 102. The portable terminal 102 displays the acquired patient information on the monitor in a predetermined format (for example, a list format). The user watches this display on the monitor to check the dosage-scheduled patients.

[Dispensing Processing at Facilities]

In the facility 100, when medicines delivered from the pharmacy 10 are dispensed to patients (medicine takers), two-dimensional codes attached to packaging bags (two-dimensional codes printed on the labels of the packaging bags) are read out by the portable terminal 102. At this time, the patients are identified, and the two-dimensional codes are read out. The identification of a patient is performed by displaying a list of resident patients in the facility on the monitor of the portable terminal 102 and selecting the patient on the screen.

The read-out two-dimensional codes are decoded and transmitted to the management server 200 together with the patient information. The two-dimensional codes given to the packaging bags are decoded to acquire medicine identification information. When receiving the patient information and the medicine identification information, the management server 200 determines the success or failure in medicine dispensing based on the management database. In other words, the success or failure in medicine dispensing is determined by determining whether or not the received patient information and medicine identification information match the information registered in the management database. The management server 200 transmits the determination result to the portable terminal 102. The portable terminal 102 displays the received determination result on the monitor. The user watches this display on the monitor to determine the success or failure in medicine dispensing.

Further, when the management server 200 determines that the medicine dispensing is correct, the management server 200 updates the item of the dosage status in the management database. In other words, the management server 200 changes the item of the dosage status from the "untaken" state to the "taken" state.

[Processing of Checking Medicine Receipt Status at Pharmacies]

In the pharmacy 10, the receipt status of the medicines which have been delivered to the facility 100 can be checked by using the one-dose-packaging audit support device 16. The one-dose-packaging audit support device 16 accepts an instruction of a check request for the medicine receipt status from the user, and executes the processing of checking the receipt status.

The acceptance of the instruction of the check request for the medicine receipt status is performed by calling a check screen for the medicine receipt status from the menu screen.

When the check screen for the medicine receipt status is called, delivery identification information on medicines which have been shipped is displayed in the form of a list as a delivery history. In addition, a receipt status is displayed for each delivery identification information.

Further, when the check screen for the receipt status is called, delivery identification information in an unreceived state is detected. Then, a check request for the receipt status is made with respect to the delivery of the detected delivery identification information.

When receiving the check request for the receipt status, the management server 200 refers to the management database to acquire information on the receipt status of the corresponding delivery identification information, and transmits the acquired information to the one-dose-packaging audit support device 16.

The one-dose-packaging audit support device 16 updates the display of the delivery history based on the received receipt status information. In other words, with respect to the item of the receipt status of each delivery identification information, if the medicines have been received, the item is changed to "received". The user watches this display of the delivery history to check the receipt status.

[Processing of Checking Dosage Status at Pharmacies]

In the pharmacy 10, the dosage status of the medicines which have been delivered to the facility 100 can be checked by using the one-dose-packaging audit support device 16. The one-dose-packaging audit support device 16 accepts an instruction of a check request for the dosage status from the user, and executes the processing of checking the dosage status.

The acceptance of the instruction of the check request for the dosage receipt status is performed by calling a check screen for the dosage status from the menu screen. When the check screen for the dosage status is called, a list of facilities which have delivered medicines is displayed. When one of the listed facilities is selected, a list of resident patients in a selected facility is displayed. Further, when one person is selected from the listed patients, a list of medicine identification information of medicines which have been delivered to the patient from the pharmacy is displayed as a dosage history of the patient. In addition, a dosage status is displayed for each medicine identification information.

Further, when a patient is selected, medicine identification information in an untaken state is detected, and a check request for the dosage status is made with respect to medicines of the detected medicine identification information.

When receiving the check request for the dosage status, the management server 200 refers to the management database to acquire information on the dosage state of the corresponding medicine identification information. The management server 200 transmits the acquired information to the one-dose-packaging audit support device 16.

The one-dose-packaging audit support device 16 updates the display of the dosage history based on the received dosage status information. In other words, with respect to the item of the dosage status of each medicine identification information, when a medicine has been taken, the item is changed to "taken". The user watches this display of the dosage history to check the dosage status of the patient.

As described above, according to the medicine management system 1 of the present embodiment, the receipt status and the dosage status of the medicines which have been delivered from the pharmacy 10 can be checked at the pharmacy 10 as the delivery source. As a result, medicines can be prevented from remaining, and it is possible to appropriately dispense medicines to patients.

Modifications

[Modification of Management Server]

The management server 200 can also be configured as a so-called cloud server. In other words, the management server 200 may be configured so that various functions provided by the management server 200 are provided by cloud computing.

[Modification of Terminal to be Used in Facilities]

The above-described embodiment is configured so that the medicine receipt processing and the medicine dispensing processing are performed by a common terminal (portable terminal 102), but it may be configured so that the medicine receipt processing and the medicine dispensing processing may be performed by different terminals. In other words, the medicine receipt processing may be performed by a terminal (first terminal) dedicated to the receipt processing while the medicine dispensing processing is performed by a terminal (second terminal) dedicated to the medicine dispensing processing.

Further, the above-embodiment may be configured so that the user ID of the terminal is assigned at the pharmacy side or assigned upon a petition from the facility side. Further, the above-described embodiment may be configured so that unique identification information (for example, a media access control address (MAC address) or the like) assigned to hardware of a terminal is used.

[Modification of Terminal Equipped in Pharmacy]

The above-described embodiment is configured so that the processing for checking the receipt status and the processing for checking the dosage status are performed by the one-dose-packaging audit support device 16, but it may be performed so that these processing is performed by another device (third terminal). For example, the above-described embodiment may be configured so that a computer having a communication function (for example, a portable terminal such as a smartphone or a tablet type terminal) is prepared in the pharmacy 10, and the check processing for the receipt status and the check processing for the dosage status are performed by the computer. In this case, a program for executing the check processing for the receipt status and the check processing for the dosage status is installed in the computer.

Further, the above-described embodiment may be configured so that the processing of uploading information to the management server 200 is also performed by the computer.

[Modification of Medicine Identification Information]

The above-describe embodiment is configured so that the medicine identification information is encoded with a two-dimensional code and displayed, but it may be configured so that the medicine identification information may be displayed as it is without being encoded. Further, the above-described embodiment may be configured so that the medicine identification information is encoded with another code such as one-dimensional code (bar code) and displayed. Further, the medicine identification information may be recorded on an electronic tag attached to (embedded in) the packaging bag. In this case, it is preferable that the electronic tag is of a type that writing can be performed on a memory area only once, and thereafter only reading from the memory can be performed.

[Modification of Delivery Identification Information]

The above-describe embodiment is configured so that the delivery identification information is encoded with a two-dimensional code and displayed, but it may be configured so that the delivery identification information may be displayed as it is without being encoded. Further, the above-described embodiment may be configured so that the delivery identification information is encoded with another code such as a one-dimensional code (bar code) and displayed. Still further, the delivery identification information may be recorded on an electronic tag attached to a delivery article which is delivered together with medicines.

The above-described embodiment is configured so that the delivery identification information is displayed on a printed matter which is delivered together with medicines (in the above embodiment, a printed matter on which a list of delivery-scheduled medicines is printed), but a target on which the delivery identification information is indicated is not limited to the above printed matter. For example, the above-described embodiment may be configured so that the delivery identification information may be indicated on a case in which medicines are stored.

Further, when a document in which patient, prescription information, dosage periods, etc. are summarized is created and delivered together with medicines, the delivery identification information may be indicated (printed) on the document.

[Modification of Acquisition of Receipt-Scheduled Medicine Information]

The above-described embodiment is configured so that the check request for receipt-scheduled medicines is made to the management server 200 by the user's operation, but it may be configured so that the check request for receipt-scheduled medicines may be made automatically. For example, it may be configured so that the management server 200 is automatically accessed at a predetermined time or at a constant time interval to make a check request.

Further, the above-described embodiment may be configured so that when there are receipt-scheduled medicines, the management server 200 notifies the portable terminal 102 of the existence of the receipt-scheduled medicines. For example, the management server 200 may be configured to notify a delivery destination of the existence of receipt-scheduled medicines at the stage when the registration of information in the management database is completed.

Further, the above-described embodiment is configured so that the information on the receipt-scheduled medicines and the delivery identification information are notified from the management server 200, and displayed, but it may be configured so that only one of the two pieces of information is notified and displayed. Further, the above-described embodiment may also be configured so that only the existence of the receipt-scheduled medicines is notified and displayed.

[Modification of Display of Dosage-Scheduled Patients]

With respect to the display of a result when the check request for dosage-scheduled patients is made by the portable terminal 102 provided in the facility 100, for example, in addition to a mode for displaying a list of patients (medicine takers) for each dosage timing, dosage timings may be displayed for each patient. When the dosage information is displayed for each patient, for example, the information on the dosage timings for each patient is acquired from the management server 200, and displayed on the monitor of the portable terminal 102. When a list of patients is displayed for each dosage timing, for example, the information on patients for each dosage timing is acquired from the management server 200, and displayed on the monitor of the portable terminal 102.

[Modification 1 of Medicine Dispensing Processing]

In the above-described embodiment, the method of identifying patients during medicine dispensing is configured so that a list of patients is displayed on the monitor of the portable terminal 102 and a patient to whom medicines are dispensed is selected. The method for identifying the patient to whom medicines are dispensed is not limited to the above manner. For example, the method may be configured so that unique identification information (medicine taker identification information) such as an ID number is assigned to each resident patient in the facility 100, and the identification information is read to identify the patient. The patient identification information may be encoded with a two-dimensional code or the like, and read out by the portable terminal 102 to identify the patient. Further, with respect to this patient identification information (including information which is encoded with a two-dimensional code), by giving the patient identification to an item which is close to the patient (for example, patient's nameplate, patient's possession, bedside, or the like), the patient can be easily identified when taking medicines.

Furthermore, the patient identification information may be issued and managed on the pharmacy side. For example, when a resident patient in a facility uses a pharmacy for the first time, identification information may be issued on the pharmacy side, and delivered to the facility.

[Modification 2 of Medicine Dispensing Processing]

When a list of patients is displayed at the time of medicine dispensing to select a patient to whom medicines are dispensed, the display of patients for whom medicine dispensing has been completed may be turned off in sequence. Alternatively, the patients for whom medicine dispensing has been completed and patients for whom medicine dispensing has not been completed may be displayed so as to be distinguishable with each other.

[Modification 3 of Medicine Dispensing Processing]

The above embodiment is configured so that when medicine dispensing is performed, a result indicating the success or failure in medicine dispensing is transmitted from the management server 200 to the portable terminal 102 of the facility 100 and displayed on the monitor. However, it may be configured so that information on medicines to be taken by a patient may be received from the management server 200 together with the result indicating the success or failure in medicine dispensing, and displayed on the monitor.

Alternatively, when a patient is identified by the portable terminal 102 at the time of medicine dispensing, information on medicines which are scheduled to be taken by the patient may be displayed on the monitor. In this case, at the stage when the patient is identified, a notification request for the information on the medicines which are scheduled to be taken by the patient is transmitted from the portable terminal 102 to the management server 200. In response to the notification request, the management server 200 searches the information on the medicines scheduled to be taken by the patient from the management database, and notifies the information to the portable terminal 102.

[Modification of Check Processing for Medicine Receipt Status]

The above-described embodiment may be configured so that the check processing for medicine receipt status to be performed at the pharmacy 10 is executed individually on a delivery basis. For example, it may be configured so as to specify delivery identification information, inquiry of the management server 200 about the receipt status, and acquire the result thereof

[Modification of Check Processing for Dosage Status]

The above-described embodiment may be configured so that the check processing for the dosage status to be performed at the pharmacy 10 is performed individually on a packaged medicine basis. For example, it may be configured so as to specify medicine identification information, inquire of the management server 200 about the dosage status, and acquire the result thereof

[Example of Portable Terminals Equipped in Facilities]

Figure 12:
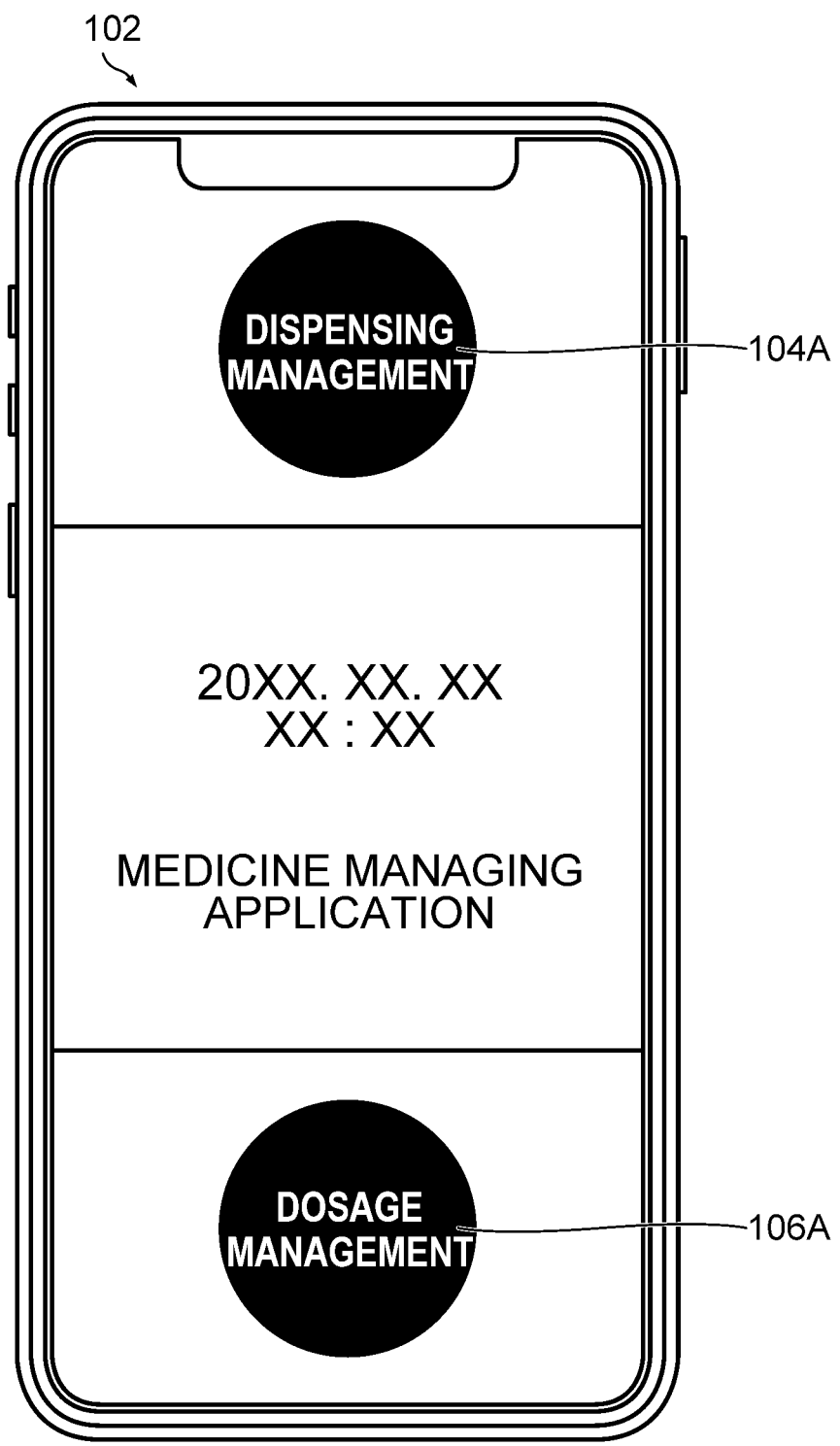
FIG. 12 is a front view showing an example of a portable terminal equipped in facilities.

FIG. 12 is a front view showing an example of a portable terminals equipped in facilities.

The portable terminal 102 of this example is configured as a terminal (first terminal and second terminal) for performing receipt processing, medicine dispensing processing, display processing of receipt-scheduled medicines, display processing of dosage-scheduled patients, and the like, and includes a smartphone. A predetermined control program (called a medicine management application) is installed in the smartphone constituting the portable terminal 102, and the above processing can be performed by executing this control program (medicine management application).

FIG. 12 shows an initial screen when the medicine management application is started. A main screen of the medicine management application is displayed on the initial screen. The current date and time is displayed on the main screen, and also a medicine dispensing management button 104A for performing medicine dispensing management and a dosage management button 106A for performing medicine dosage management are displayed on the main screen.

Figure 13:
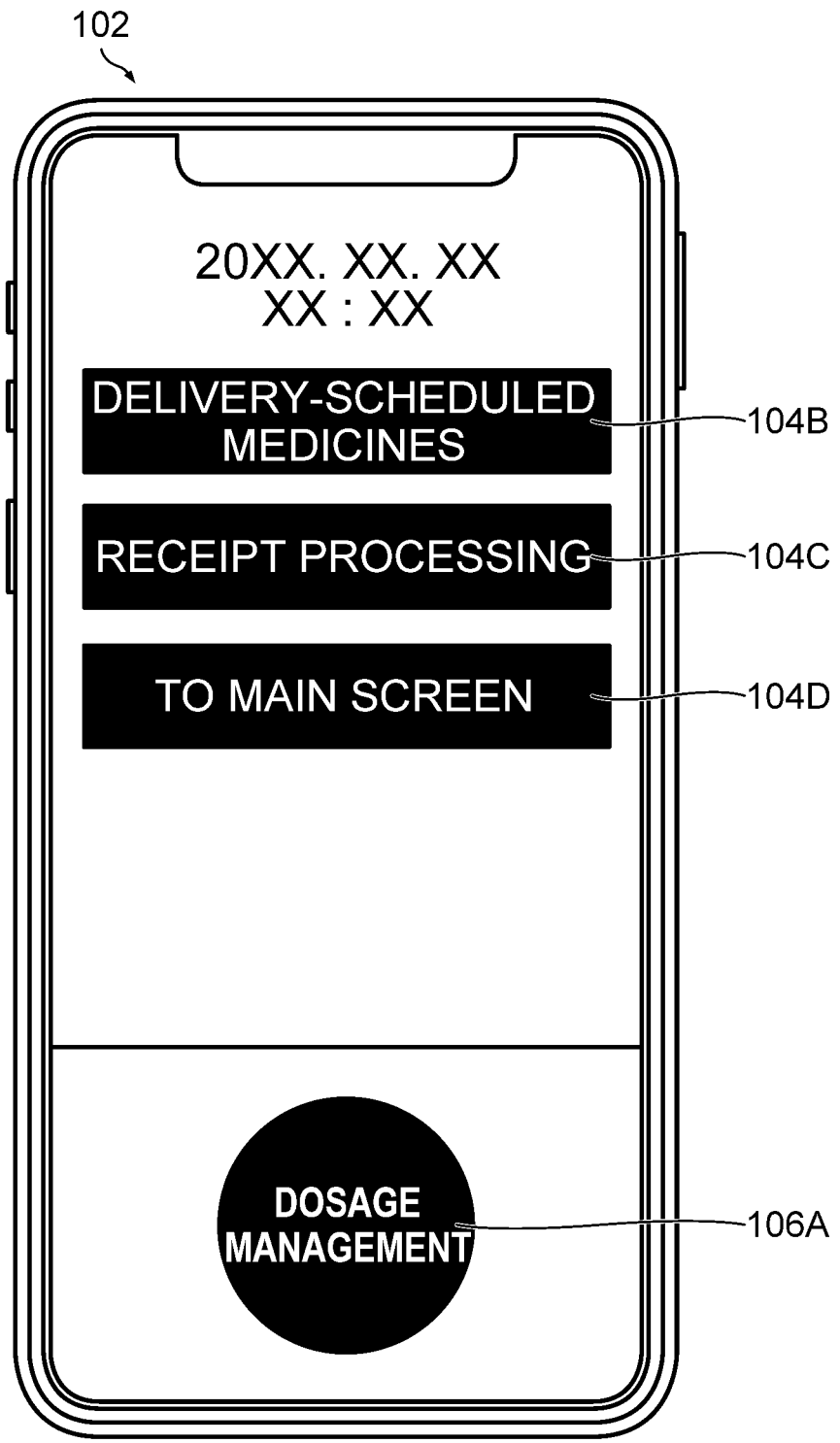
FIG. 13 is a front view of the portable terminal in a state where a medicine dispensing management screen is displayed.

FIG. 13 is a front view of the portable terminal in a state where the screen of the medicine dispensing management is displayed.

When the medicine dispensing management button 104A is touched, the screen of the portable terminal 102 is switched to the screen of the medicine dispensing management. Not only the current date and time and the dosage management button 106A are displayed on the screen of the medicine dispensing management, but also a medicine dispensing management first button 104B, a medicine dispensing management second button 104C, and a medicine dispensing management third button 104D are displayed on the screen of the medicine dispensing management.

The medicine dispensing management first button 104B is a button for performing the processing of acquiring information on receipt-scheduled medicines. When the medicine dispensing management first button 104B is touched, the processing of the check request for receipt-scheduled medicines is performed on the management server 200, and the result thereof is displayed on the monitor.

The medicine dispensing management second button 104C is a button for performing the receipt processing. When the medicine dispensing management second button 104C is touched, the portable terminal 102 is switched to a reading mode for two-dimensional codes. The user reads a two-dimensional code by using a camera to execute the receipt processing.

The medicine dispensing management third button 104D is a button for returning to the main screen. When the medicine dispensing management third button 104D is touched, the display of the screen is switched to the main screen (see FIG. 12).

Figure 14:
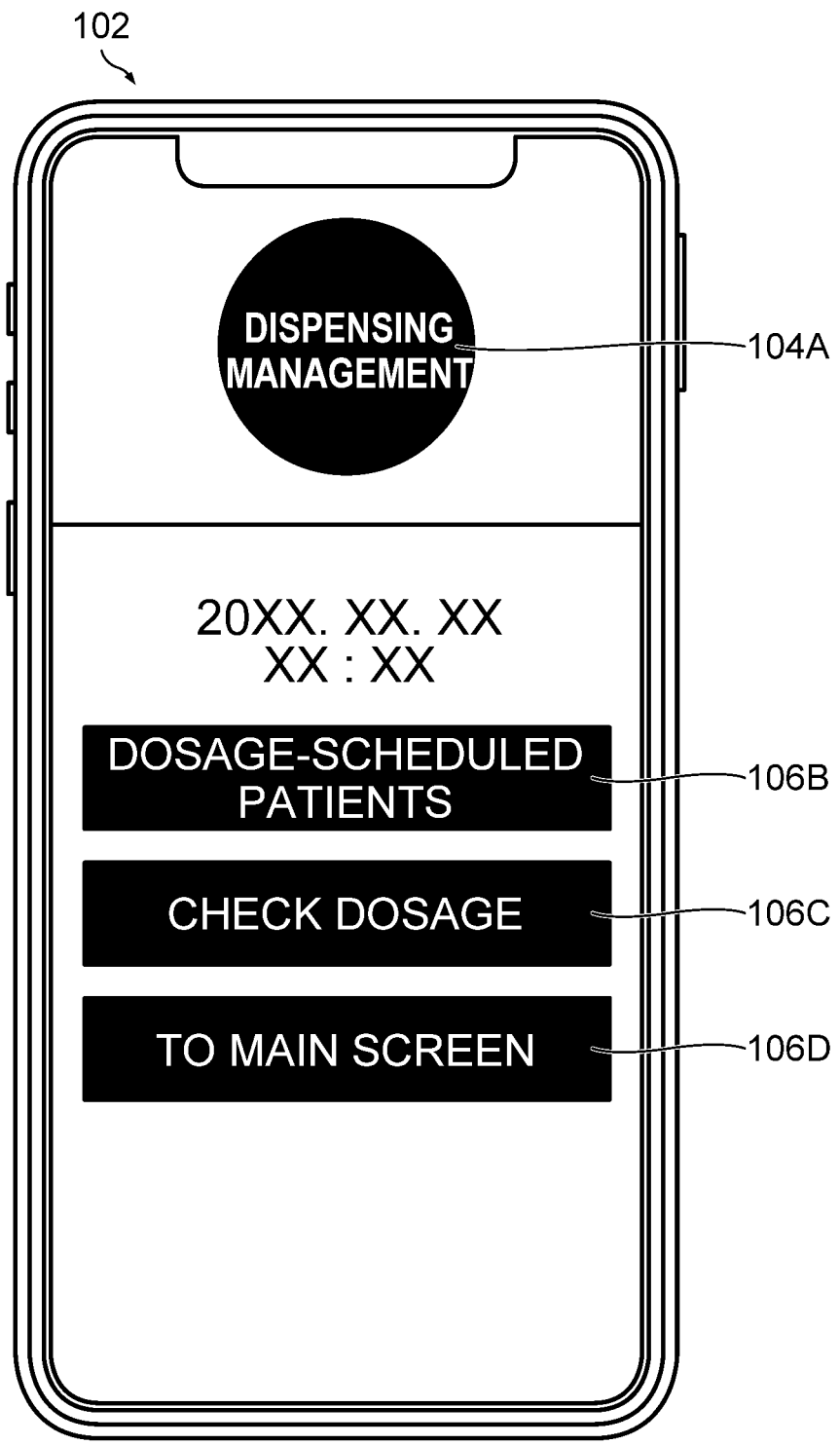
FIG. 14 is a front view of the portable terminal in a state where a dosage management screen is displayed.

When the dosage management button 106A is touched on the screen of the medicine dispensing management, the display of the screen is switched to the screen of the dosage management (see FIG. 14).

FIG. 14 is a front view of the portable terminal in a state where the screen of the dosage management is displayed.

When the dosage management button 106A is touched, the screen of the portable terminal 102 is switched to the screen of the dosage management. The current date and time and the medicine dispensing management button 104A are displayed on the screen of the dosage management, and also a dosage management first button 106B, a dosage management second button 106C, and a dosage management third button 106D are display on the screen of the dosage management.

The dosage management first button 106B is a button for performing the processing of acquiring information on dosage-scheduled patients. When the dosage management first button 106B is touched, the processing of a check request for dosage-scheduled patients is performed on the management server 200, and the result thereof is displayed on the monitor.

The dosage management second button 106C is a button for performing the dosage processing. When the dosage management second button 106C is touched, the portable terminal 102 is switched to the reading mode for two-dimensional codes. The user reads a two-dimensional code by using the camera and performs the dosage processing.

The dosage management third button 106D is a button for returning to the main screen. When the dosage management third button 106D is touched, the display of the screen is switched to the main screen (see FIG. 12).

When the medicine dispensing management button 104A is touched on the screen of the dosage management, the display of the screen is switched to the screen of the medicine dispensing management (see FIG. 13).

Figure 15:
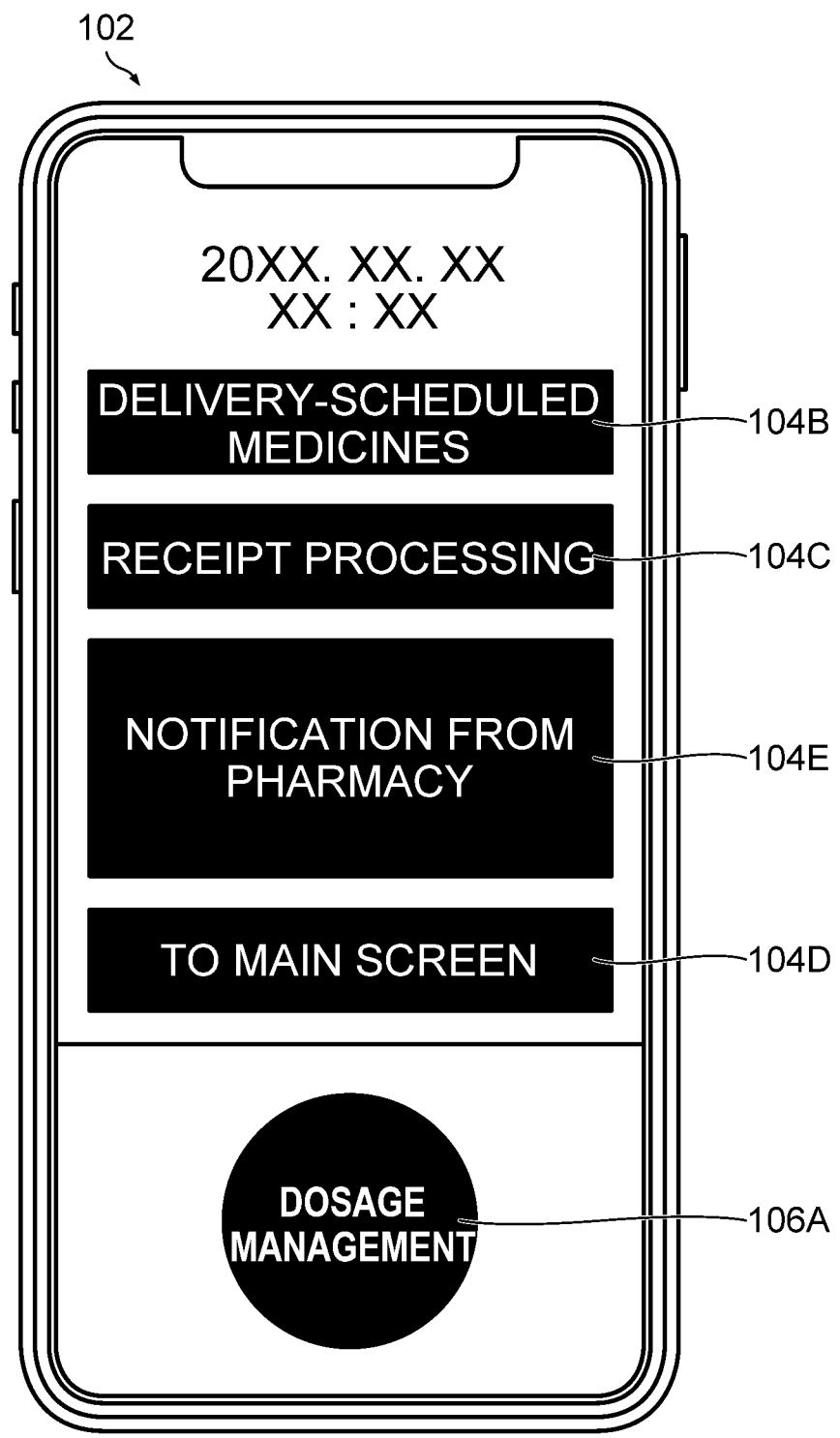
FIG. 15 is a diagram showing another example of the medicine dispensing management screen.

FIG. 15 is a diagram showing another example of the medicine dispensing management screen.

As shown in FIG. 15, a message display field 104E is displayed on the screen of the medicine dispensing management of this example. A message transmitted from a pharmacy is displayed in the message display field 104E. The message from the pharmacy is transmitted from the one-dose-packaging audit support device 16 to the portable terminal 102 via the management server 200. When a destination (facility) is designated and a message is input in the one-dose-packaging audit support device 16, the message is stored in the management server 200. When the user of the portable terminal 102 touches the medicine dispensing management button 104A, the portable terminal 102 accesses the management server 200 to check the presence or absence of a message. When there is a message, the portable terminal 102 receives the message, and displays it in the message display field 104E.

Figure 16:
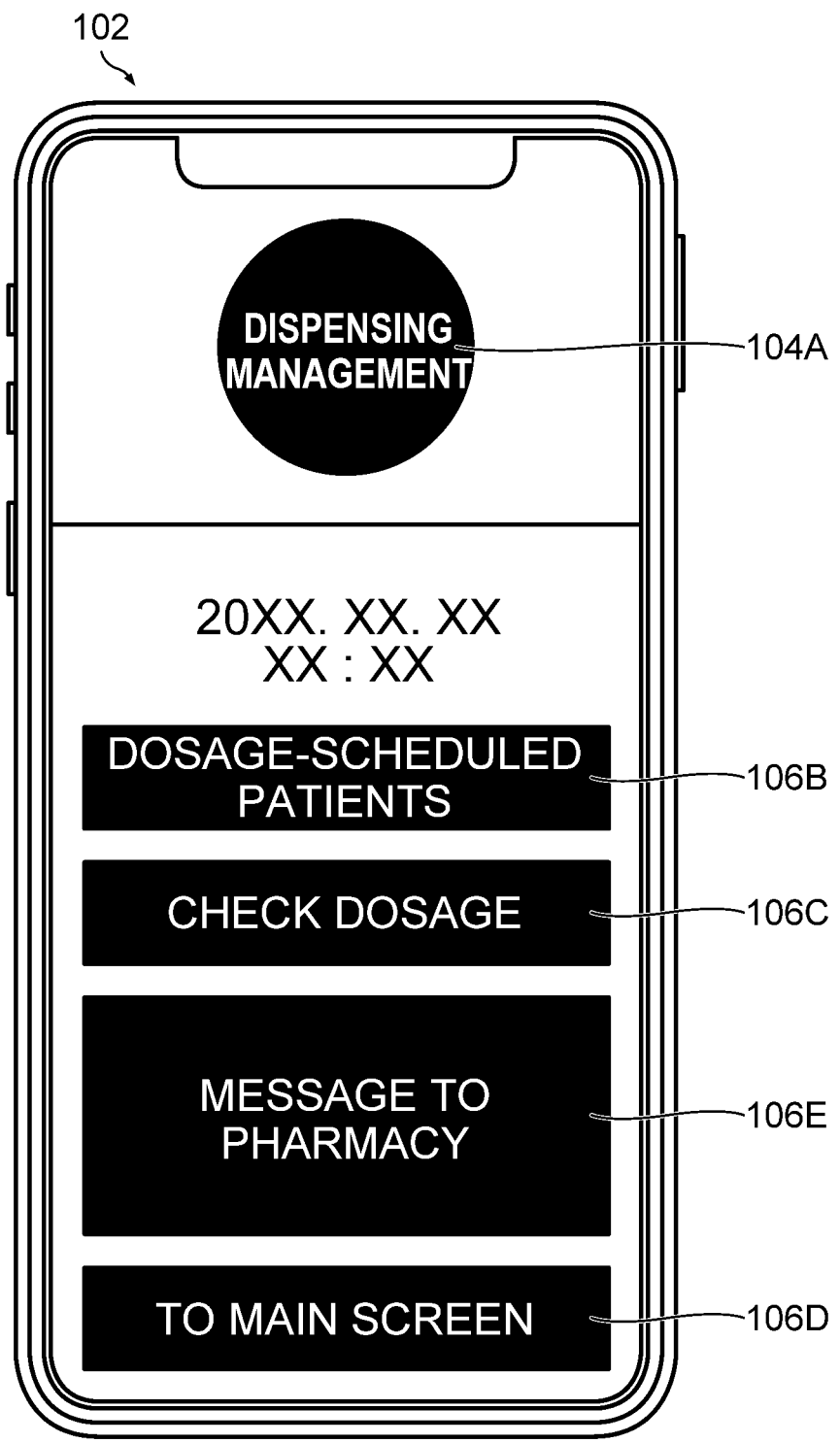
FIG. 16 is a diagram showing another example of the dosage management screen.

FIG. 16 is a diagram showing another example of the screen of the dosage management.

As shown in FIG. 16, the screen of the dosage management of this example is provided with a message input field 106E. A message is input from the facility to the pharmacy in the message input field 106E. Character input means provided in the portable terminal 102 is used for inputting a message. The input message is notified to the one-dose-packaging audit support device 16 via the management server 200.

[Modification of Delivery Source]

In the above embodiment, a case where the receipt status and the dosage status for medicines to be delivered from the pharmacy has been described as an example, but the delivery source of the medicines is not limited to the above case. The present invention can also be applied to a case where medicines are delivered from a hospital pharmacy, and the like. In addition, the present invention can also be applied to a case where medicines are delivered from a predetermined delivery center or the like.

[Others]

The present system may be a system connected to electronic clinical records, clinical test values, test images, etc. by a network, and establish data cooperation with other cloud storage service systems such as regional medical cooperation and long-term care cooperation, thereby enabling mutual data provision.

The functions of the first terminal, the second terminal, and the third terminal can be implemented by using various processors. The various processors include, for example, CPU (Central Processing Unit), which is a general-purpose processor for executing software (programs) to implement various functions. Further, the various processors described above include a graphics processing unit (GPU) which is a processor specialized for image processing, and a programmable logic device (PLD) such as a field programmable gate array (FPGA) which is a processor whose circuit configuration can be changed after manufacturing. Further, the above-mentioned various processors also include a dedicated electric circuit which is a processor having a circuit configuration specially designed for executing specific processing such as an application specific integrated circuit (ASIC).

When the above-mentioned processor or electric circuit executes software (program), processor-(computer-)readable codes of software to be executed are prestored in a non-transient recording medium such as a read only memory (ROM), and the processor refers to the software. The software to be prestored in the non-transient recording medium includes a program for executing an imaging method according to the present invention (a program for operating the imaging device according to the present invention). The codes may be recorded in a non-transient recording medium such as each type of optical magnetic recording device or a semiconductor memory instead of ROM. In processing using software, for example, a random access memory (RAM) is used as a temporary storage area, and for example, data stored in an electronically erasable and programmable read only memory (EEPROM) (not shown) may be referred to.

Furthermore, the present invention is not limited to the above-described embodiment, and it goes without saying that various modifications can be made without departing from the spirit of the present invention.

EXPLANATION OF REFERENCES 1 medicine management system
2 network
10 pharmacy
12 receipt computer
14 packaging device
16 one-dose-packaging audit support device
16A one-dose-packaging audit support device main body
16A1 imaging unit
16A2 label printing unit
16B computer
16B1 prescription information acquiring unit
16B2 imaging control unit
16B3 audit support unit
16B4 medicine identification information giving unit
16B5 delivery processing unit
16B6 delivery identification information giving unit
16B7 audit result recording unit
16B8 label print control unit
16B9 print control unit
16B10 upload unit
16B11 receipt status check processing unit
16B12 dosage status check processing unit
16C touch panel monitor
16D printer
100 facility
102 portable terminal
102A receipt processing unit
102B dosage processing unit
102C receipt-scheduled medicine display processing unit
102D dosage-scheduled patient display processing unit
104A medicine dispensing management button
104B medicine dispensing management first button
104C medicine dispensing management second button
104D medicine dispensing management third button
104E message display field
106A dosage management button
106B dosage management first button
106C dosage management second button
106D dosage management third button
106E message input field
200 management server
200A registration processing unit
200B receipt status managing unit
200C dosage status managing unit
200D receipt status notification processing unit
200E dosage status notification processing unit
200F receipt-scheduled medicine notification processing unit
200G dosage-scheduled patient notification processing unit
L label
L1 dosage-scheduled date
L3 dosage timing
Lc two-dimensional code
P packaging bag
S10 to S14 procedure of processing to be performed at pharmacy before medicines have been delivered
S12a to S12h procedure of processing when audit is performed by using one-dose-packaging audit support device
S13a to S13e procedure of preparing for delivery

What is claimed is:
1. A medicine management system comprising:
a management server configured to manage a receipt status and a dosage status of medicines to be delivered;
a first terminal configured to have a function of notifying the management server of information indicating receipt of the medicines when the medicines have been received;
a second terminal configured to have a function of notifying the management server of information indicating dosage of the medicines when the medicines have been taken; and
a third terminal configured to have a function of acquiring from the management server and displaying information on a receipt status and a dosage status of the medicines,
wherein the medicines include packaged medicines which are packaged on a dose basis based on prescription information, and unique delivery identification information is given to the medicines for each delivery,
the delivery identification information is indicated on a delivery article to be delivered together with the medicines,
unique medicine identification information is given to the packaged medicines on a package basis, and indicated on an individual packaging bag,
the management server manages the medicine identification information in association with the delivery identification information and information extracted from the prescription information, the first terminal reads the delivery identification information indicated on the delivery article, and notifies the management server of information indicating the receipt, the second terminal reads the medicine identification information indicated on the packaging bag, and notifies the management server of information indicating the dosage of the medicines, and the management server receives a notification of the information indicating the receipt from the first terminal to manage the receipt status of the medicines, and receives a notification of the information indicating the dosage from the second terminal to manage the dosage status of the medicines.

2. The medicine management system according to claim 1, wherein the first terminal further has a function of acquiring from the management server and displaying the delivery identification information and information of the medicines scheduled to be delivered.

3. The medicine management system according to claim 1, wherein the second terminal further has a function of acquiring from the management server and displaying information on a medicine taker who is scheduled to take a medicine.

4. The medicine management system according to claim 1, wherein the second terminal further has a function of acquiring from the management server and displaying information on a dosage timing for each medicine taker.

5. The medicine management system according to claim 1, wherein the second terminal further has a function of acquiring from the management server and displaying information on a medicine taker for each dosage timing.

6. The medicine management system according to claim 1, wherein the second terminal identifies a medicine taker, read the medicine identification information, and notifies the management server of information indicating the medicine dosage.

7. The medicine management system according to claim 1, wherein the second terminal reads medicine taker identification information unique to a medicine taker, reads the medicine identification information, and notifies the management server of information indicating the dosage.

8. The medicine management system according to claim 1, wherein the delivery identification information is encoded and indicated on the delivery article.

9. The medicine management system according to claim 1, wherein the medicine identification information is encoded and indicated on the packaging bag.

10. The medicine management system according to claim 1, wherein the first terminal also serves as the second terminal.

11. The medicine management system according to claim 1, further comprising a one-dose-packaging audit support device including:
an imaging unit configured to image the packaged medicines on a package basis;
an audit support unit configured to support audit of the packaged medicines based on images captured by the imaging unit and the prescription information; and
a medicine identification information giving unit configured to give, on a package basis, the medicine identification information to the packaged medicines for which audit has been completed.

12. The medicine management system according to claim 11, wherein the one-dose-packaging audit support device further includes a medicine identification information transmission unit configured to transmit the medicine identification information to the management server in association with information extracted from the prescription information.

13. The medicine management system according to claim 11, wherein the one-dose-packaging audit support device further includes:
a delivery identification information giving unit configured to give the delivery identification information; and
a delivery identification information transmitting unit configured to transmit the medicine identification information to the management server in association with the delivery identification information.

14. The medicine management system according to claim 13, wherein the one-dose-packaging audit support device further includes a printing unit configured to print the delivery identification information.

15. The medicine management system according to claim 11, wherein the one-dose-packaging audit support device also serves as the third terminal.

16. The medicine management system according to claim 1, wherein the management server manages a receipt status and a dosage status of medicines to be delivered from a pharmacy or a hospital pharmacy.

* * * * *